(12) United States Patent
Segura Puello

(10) Patent No.: US 9,056,070 B2
(45) Date of Patent: Jun. 16, 2015

(54) AUTOLOGOUS BIOLOGICAL CANCER VACCINE

(75) Inventor: Hugo Ramiro Segura Puello, Bogota (CO)

(73) Assignee: Universidad Manuela Beltran, Bogota (CO)

( * ) Notice: Subject to any disclaimer, the term of this patent is extended or adjusted under 35 U.S.C. 154(b) by 0 days.

(21) Appl. No.: 13/695,062

(22) PCT Filed: Apr. 27, 2010

(86) PCT No.: PCT/IB2010/000977
§ 371 (c)(1),
(2), (4) Date: Oct. 29, 2012

(87) PCT Pub. No.: WO2011/135393
PCT Pub. Date: Nov. 3, 2011

(65) Prior Publication Data
US 2013/0045235 A1 Feb. 21, 2013

(51) Int. Cl.
*A61K 39/00* (2006.01)
*A61K 39/23* (2006.01)

(52) U.S. Cl.
CPC .............. *A61K 39/0011* (2013.01); *A61K 39/23* (2013.01); *A61K 2039/5254* (2013.01); *A61K 2039/55511* (2013.01); *A61K 2039/55588* (2013.01)

(58) Field of Classification Search
None
See application file for complete search history.

(56) References Cited

U.S. PATENT DOCUMENTS

| | | | | |
|---|---|---|---|---|
| 4,537,769 | A * | 8/1985 | Cerini | 424/210.1 |
| 5,709,879 | A * | 1/1998 | Barchfeld et al. | 424/450 |
| 8,142,795 | B2 * | 3/2012 | Francon et al. | 424/218.1 |
| 8,357,376 | B2 * | 1/2013 | Liu et al. | 424/209.1 |
| 2009/0117081 | A1 | 5/2009 | Meyers et al. | |
| 2009/0162405 | A1 | 6/2009 | Qian | |

FOREIGN PATENT DOCUMENTS

| | | |
|---|---|---|
| CO | 5930064 A1 | 6/2008 |
| EP | 1221959 B1 | 7/2002 |
| EP | 1523989 A1 | 4/2005 |
| EP | 1576966 A1 | 9/2005 |
| EP | 2075003 A1 | 7/2009 |
| WO | 0130366 A2 | 5/2001 |
| WO | 2004007734 A1 | 1/2004 |
| WO | 2009066824 A1 | 5/2009 |
| WO | 2009083202 A1 | 7/2009 |

OTHER PUBLICATIONS

Povey et al, Can. Vet. J., 1983;24:245-248.*
Lo-Man et al, Eur. J. Immunol, 1998; 28:1401-1407.*
Boisgerault et al, J Immunol, 2005;174:3432-3439.*
Spohn and Bachman, Expert Rev Vaccines, 2008; 7:43-54.*
Jiang et al, Cancer Biother. Radiopharm., 2000; 15:495-506.*
Nobivic tech sheet Parvovirus Canino, Apr. 2009.*
E. Martinez et al., Marcadores tumorales circulantes con valor pronostico (Circulating tumour markers of prognostic value), ANALES Sis San Navarra 2000 (vol. 24, Supl. 1) pp. 53-61, Introduction and 1 table. Cited in PCT Int'l Search Report. English Abstract included as separate sheet.

* cited by examiner

*Primary Examiner* — Mark Halvorson
(74) *Attorney, Agent, or Firm* — Steve Witters; The Juhasz Law Firm

(57) ABSTRACT

The present disclosure relates to an autologous biological cancer vaccine and to a method for preparing the same. The vaccine of the present application is a biological vaccine obtained from overexpressed proteins in the serum of cancer patients, proteins to which have been added immunological adjuvants such as an attenuated virus DNA and amino acids in order to cause an immune response, blocking tumor cells. The preparation method includes obtaining the antigen associated with the tumor as well as the vaccine preparation with attenuated virus DNA, combining the components under conditions that have been determined by experimentation, filtration and refrigeration.

18 Claims, 25 Drawing Sheets

US 9,056,070 B2

AUTOLOGOUS BIOLOGICAL CANCER VACCINE

CLAIM TO PRIORITY

This application is a continuation of, and claims the benefit of, PCT/IB2010/000977 (PCT published application WO2011/135393), filed Apr. 27, 2010, and which is hereby incorporated by reference in its entirety.

FIELD

The field of the disclosure is that of anti-cancer vaccines, and specifically anti-cancer vaccines that reactivate a patient's immune system without deleterious side effects.

BACKGROUND

The knowledge developed about the immune system in the twentieth century and today, has allowed its use in cancer treatment, scientists around the world indicate it has been possible to reactivate the immune system with immunotherapy, mainly from vaccines with which it has proven possible to block tumor cells and provide quality of life and survival to patients treated with such vaccines. It is also known that conventional treatments such as chemotherapy and radiotherapy do not "cure" cancer, but are palliative therapies with many side effects in almost all body systems, causing in turn what has been called the "second tumor" or metastasis and disease progression. Therefore, immunotherapy offers a new alternative in the treatment of cancer, because it does not generate the side effects of other treatments. Immunotherapy is regarded as the fourth treatment against cancer.

At present there are several known studies on cancer vaccines and some in which tumor antigens extracted through the serum of cancer patients are used, in order to boost the immune system and induce a specific immune response against tumor cells.

Each vaccine has certain components based on the type of vaccine desired: there are biological vaccines, synthetic, genetic, protein, antigen, dendritic cells, etc.

It is thought that the vaccine's action mechanism may include the inhibition of the enzyme collagenase which is employed by tumor cells to cause dissolution of collagen used by all cells to stick together. Another possible mechanism of action is that by increasing collagen concentration with the vaccine, the enzyme collagenase is inhibited and the metastasis to other organs by the tumor cells is blocked.

The vaccine is a biological compound intended to reactivate and stimulate immune system cells, B lymphocytes, T lymphocytes and NK cells to block the metastasis of tumor cells and reactivate the bone marrow depressed by the cancer itself and by conventional treatments, such as chemotherapy and radiotherapy Currently research studies have been conducted that seek to determine the behavior of the immune system in order to search for alternatives in the fight against tumor cells. Among the state of the art documents related to the present disclosure are:

European patent application EP1523989 which discloses compositions and methods for treating and/or preventing cancer in an animal. Improvements are reported with the use of a yeast-based vaccine comprising a yeast vehicle and an antigen selected to generate a humoral immune response in the animal. Said vaccine comprises yeast vehicle and a fusion protein expressed by the yeast vehicle it comprises: at least one cancer antigen and a peptide bound to the N terminal cancer antigen. The peptide with an established amino acid sequence stabilizes the fusion protein expression in the yeast vehicle or prevents translational modifications of the expressed fusion protein.

For its part, publication WO2009/066824 discloses a prophylactic and immunological therapy vaccine comprising monocytes or immature myeloid cells (IMCs) loaded with the native NK cell ligand and an antigen for the prevention and treatment of cancer, more precisely a vaccine comprising IMC monocytes loaded with α-galactosylceramide and an antigen to generate specific immune response. The antigen is obtained from the tumor and is expressed by transduction from a recombinant virus (adenovirus, retrovirus, virus vaccinia, pox-virus, Sindbis virus). Among the antigens employed are Her-2/neu, proteinase 3, a gene associated with Wilm's tumor, and murinoglobulin, and others.

European patent application EP 1576966 provides a method for the preparation of a vaccine. The method includes: (1) analyzing a specific antigen of a particular pathogen; (2) obtaining a polynucleotide encoding a specific antigen, (3) obtaining a polynucleotide sequence having a sufficient difference from the polynucleotide, (4) preparing a vaccine using the polynucleotide sequence. The antitumor vaccine corresponds in particular to an EGFR molecular vaccine, prepared from an EGRF molecule as an antigen and proteins, genes, viruses or bacteria, stably transformed. One of the biological functions of the EGFR molecular vaccines is that they possess an antitumor effect on a variety of solid tumors in which the molecule EGFR is overexpressed, i.e., lung, breast, ovarian, colon, prostate and stomach cancers among others, further comprising a protective immunological effect and therapeutic inhibition of metastatis. The vaccine generates an active and passive immune response by the organism treated.

The publication WO 2004/007734 relates to constructed plasmids that express the human Her-2/neu gene and possess anticancer activity and a vaccine comprising the same for preventing and or treating cancer. The plasmids are used as vectors that encode tumor-associated antigens. The document mentions that they are easily generated and safe to administer. Such plasmids are prepared by inserting a truncated HER-2/neu gene lacking intracellular domain into a pTV2 or pCK plasmid. The plasmids additionally translate a cytokine gene. The vaccine then comprises the plasmids prepared, a pharmaceutically acceptable carrier and a cytokine gene.

Similarly, publication WO 2009/083202 relates to a parvovirus characterized by a CpG-enriched genome, wherein the genome contains at least 2 additional CpG inserts that are not present in the natural genome, and the use of a parvovirus based on parvovirus H1, Lu lll, tiny mouse virus (MMV), mouse parvovirus (MPV), tiny rat virus (RPV), rat virus (RV), vectors based on the above species and/or cells capable of actively producing the prior species for the preparation of a pharmaceutical composition for treating cancer, specifically pancreatic carcinoma, hepatoma or lymphoma.

U.S. Pat. Appl. Publ. 2009/0117081 discloses that parvoviruses such as adeno-associated type 2 virus (AAV2) are oncolytics, selectively mediating apoptosis in cancer cells and their precursors, while leaving healthy cells intact. It further discloses a pharmaceutical composition comprising these viruses and a vehicle.

Patent application EP 1523989 relates to a process for the preparation of an anticancer vaccine derived from serum or autologous leukocytes. The preparation method includes coagulating a defined amount of blood from a cancer patient who has not been treated with chemotherapy or radiotherapy, centrifuging said blood with a rotational speed of at least 2000 rpm for 30 seconds, combining the supernatant serum with an aqueous solution of formaldehyde at a temperature of at least 37° C. for at least 28 days, treating the product of the previous step with phosphoric acid, filtering, treating the precipitate with aqueous solution of hydrochloric acid to lower the pH to 4, centrifuging the product at a rotational speed of at least 2000 rpm, collecting the precipitate, treating and dissolving the precipitate with a buffer solution to raise the pH to a physiological value and repeating the last eight steps.

Spanish patent application ES2250226 claims the use of non-pathogenic parvoviruses for the preparation of a medicament for reducing the side effects of therapies with genotoxic agents in patients with chronic and/or consumptive reduction diseases, the reduction of side effects appearing with maintenance or increase of the genotoxic agents' dose and the side effects affecting hematological parameters.

Within the state of the art are also reports of investigations conducted by Dr. Matthias Rath related to the mechanisms cancer uses to expand through the body and particularly to the mechanism of the degradation of collagen.

While the prior art has sought solutions to the technical problem, which is to provide safe and effective therapeutic alternatives and without the side effects associated with chemotherapy and radiotherapy, there are still no biological vaccines which, from tumor-associated antigen (obtained from cancer patient serum) and adjuvants such as an attenuated DNA virus, and specifically a parvovirus and specific amino acids, would allow not only treating cancer without side effects but also inhibit metastasis and provide overall quality of life and survival.

In particular it is relevant to mention that none of the mentioned antecedences reports experimental results or clinical studies proving the effectiveness of the methods and vaccines in humans. By contrast, the effectiveness of the vaccine in the present disclosure has been demonstrated in humans as will be shown later in the examples. Therefore, the vaccine in the present disclosure provides the following improvements and advantages over conventional vaccines in the prior art:

1. It comprises the parvovirus genome (PVC-2), non-pathogenic and attenuated, containing genes to direct the production of 4 or 5 proteins, three of which form the viral capsid. These viruses which have only about 5000 nucleotides are easy to sequence, so it is possible to map nucleotides; from these proteins an active cellular immunity is produced.

2. It has an antigen which is extracted through the patient's own blood (autologous), whose tumor protein is overexpressed, which provokes a humoral immunity, with production of antibodies (Ab).

3. It will not cause damage to healthy cells, but will react specifically against tumor cells.

4. It will reactivate the bone marrow (red cells, white cells and platelets) depressed by cancer and traditional treatments, which has been shown in clinical studies. It has been shown it can reactivate defenses (B lymphocytes).

5. It has three amino acids as adjuvants that will block the enzyme collagenase and/or increase collagen degraded by tumor cells, to in turn regenerate tissue damaged by the cancer itself or by the conventional treatments applied.

6. In patients treated with chemotherapy and/or radiotherapy, the vaccine can decrease the side effects caused by such traditional treatments, improving the quality of life and survival of patients, which has been shown in clinical studies of patients treated in advanced stages of the disease.

7. Unlike other vaccines, it has been tested in humans in clinical phases I and II, showing a 98% safety in patients treated. Only mild side effects have been reported such as irritation at the site of vaccine application (not in all patients) and slight erythema that subsides after a few minutes.

8. The vaccine tested in humans in clinical phase II, unlike other vaccines presented, shows effectiveness in specific types of cancer such as malignant melanoma, breast cancer, prostate cancer and hematopoietic cancers, which is advantageous, as it not only allows obtaining an immune response of humoral type (Ac), but also produces an active specific cellular immunity against tumor cells, thanks to the components that constitute the vaccine.

9. In studies of stages I and II, it was shown that during the 24 months of study and treatment of patients, it could give most of them quality of life (Karnofsky) and survival, exceeding expectations given to patients with conventional treatments.

SUMMARY OF THE DISCLOSURE

The vaccine in the present disclosure comprises the mixture of substances called "immunological adjuvants" together with the specific active ingredient, a protein that is overexpressed in cancer cells, called tumor-associated antigen (ATA). Among the adjuvants is found a virus DNA and three amino acids that will produce an immune response by stimulating and increasing proteins called interferons (alpha and gamma IFN), as well as some cytokines, such as IL-2 activating B lymphocytes, producing a humoral (antibody) and cellular immunity, increasing the lymphocytes T, Th (Lth1 and Lth2) which allow activation of cytotoxic T lymphocytes (TLC) and NK cells, from MHC I and II, in order to block and lead tumor cells normally to apoptosis. It has been shown that in the serum of cancer patients are found between 70% and 90% of overexpressed tumor proteins.

It has been found that the vaccine in the disclosure reactivates the immune system and blocks the metastases in the early stages of cancer. Similarly, it elicits an immune response against tumor cells and results in the production of new defense cells, such as B-lymphocytes (humoral immunity) and Tc, Th, NK lymphocytes (cellular immunity). Additionally it blocks the growth and spread (metastasis) of tumor cells by either inhibiting the production of the enzyme collagenase, which causes metastases of malignant cells to other tissue, or because it reactives collagen production, which is responsible for maintaining the normal and tumor cells stuck together.

The results obtained after the application of various doses of the vaccine, specifically between 1 and 10 doses during 24 months of treatment, show that the vaccine in the disclosure is capable of reactivating bone marrow in the medium and long term and is also capable of inhibiting tumor growth when another treatment has not yet been introduced. Additionally, it has been observed to also help reduce the symptoms produced by traditional therapies such as chemotherapy and/or radiotherapy.

It has also been shown that the vaccine improved the quality of life and overall survival of patients even beyond that predicted by conventional treatment according to the type of cancer at the time of treatment, and in particular for cancer types melanoma, breast cancer, leukemias and lymphomas. Statistical results allow the inference that the vaccine is safe and effective.

One embodiment of the disclosure is an autologous biological vaccine for treating cancer. The vaccine includes an active component corresponding to a tumor-associated antigen, in which a protein is overexpressed according to a type of cancer. The vaccine also includes a solvent, an attenuated virus DNA of a type parvovirus (PVC-2), and three amino acids (AA) corresponding to one essential amino acid and two nonessential amino acids.

Another embodiment is a method for preparing an autologous biological vaccine. The method includes the steps of: a. providing a tumor-associated antigen (ATA); b. providing a DNA attenuated virus vaccine; c. placing 100 to 150 ml of distilled and deionized water in a container; d. centrifuging all components at a rate between 500 and 2000 rpm; e. adding one essential and two nonessential amino acids to the distilled and deionized water that is spinning, one at a time or all at once; adding 0.2 to 0.3 ml of the DNA attenuated virus vaccine; g. adding between 0.1 ml and 0.2 ml of the tumor-associated antigen; and filtering. The container may contain a magnetic stirrer. After the step of filtering, a step of refrigerating may be carried out at −4° C.

DETAILED DESCRIPTION OF THE DISCLOSURE

Figure 1:
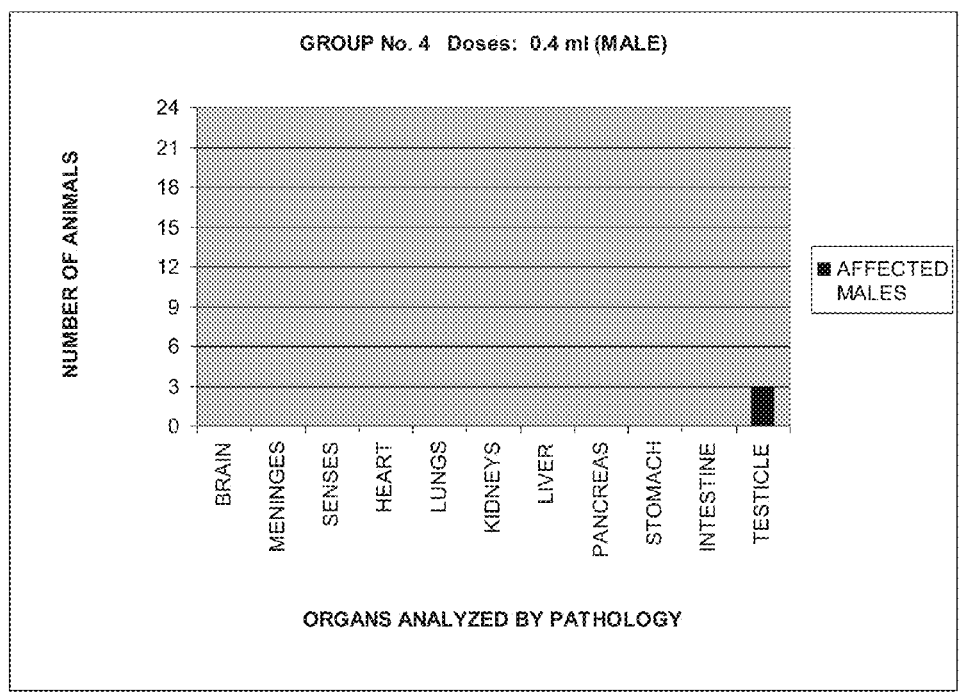
FIG. 1 shows the number of male Wistar rats affected in the testicles according to the toxicity study described in Example 2, for animal Groups 1, 2, 3 and 4.
Figure 2:
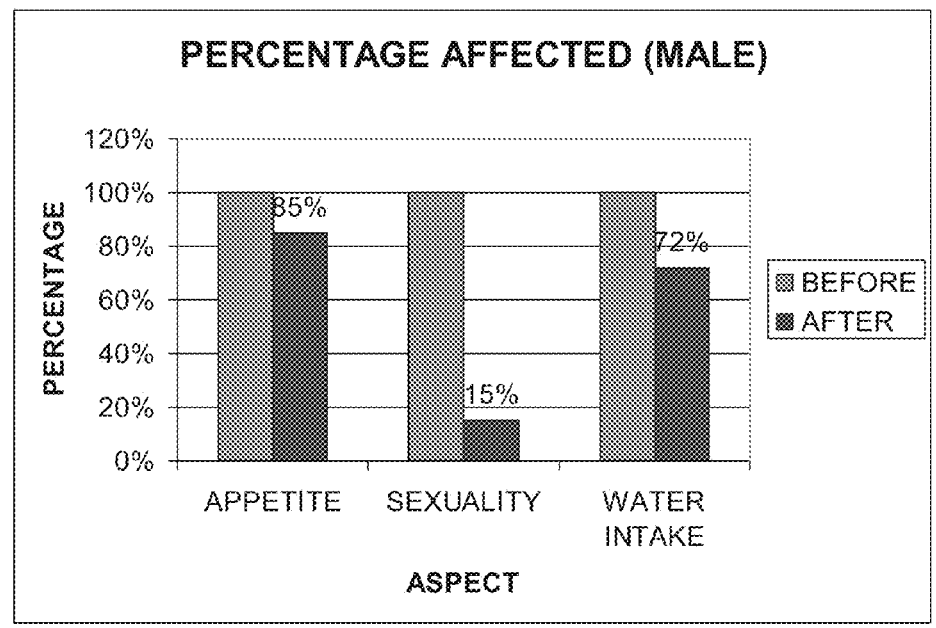
FIG. 2 shows the percentage of male Wistar rats affected for each of the trial parameters: appetite, sexuality, and water consumption, according to the toxicity study described in Example 2, for animal Groups 1, 2, 3 and 4.
Figure 3:
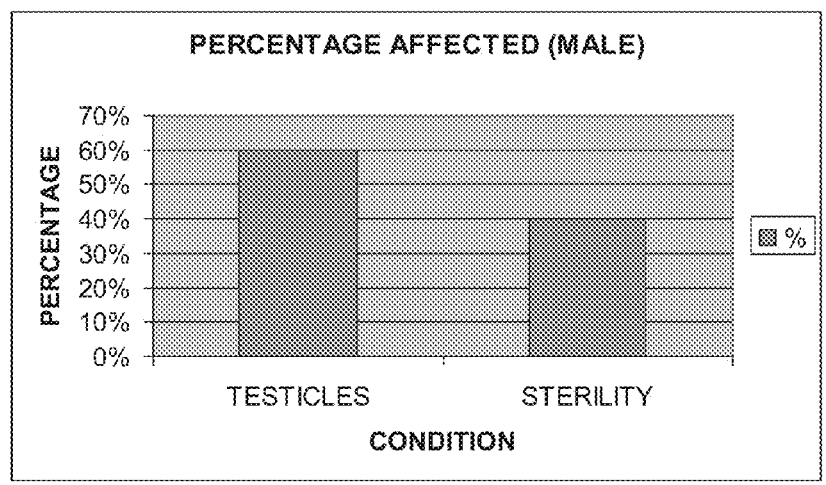
FIG. 3 reports the percentage of male Wistar rats affected for each of the trial parameters indicated: testicles and sterility, according to the toxicity study described in Example 2, for animal Groups 1, 2, 3 and 4.
Figure 4:
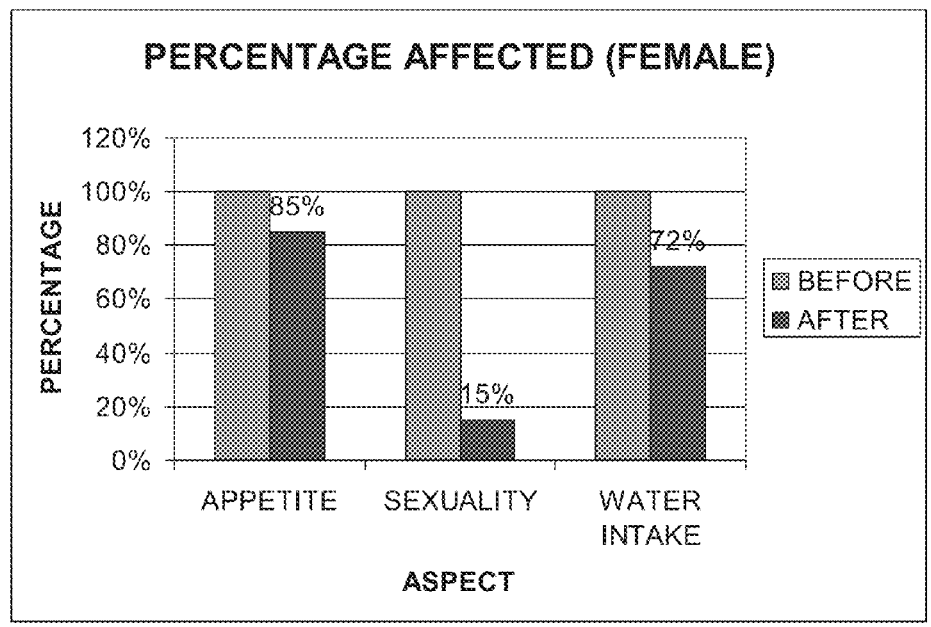
FIG. 4 describes the number of female Wistar rats affected for each of the trial parameters; appetite, sexuality, and water consumption, according to the toxicity study described in Example 2, for animal Groups 1, 2, 3 and 4.
Figure 5:
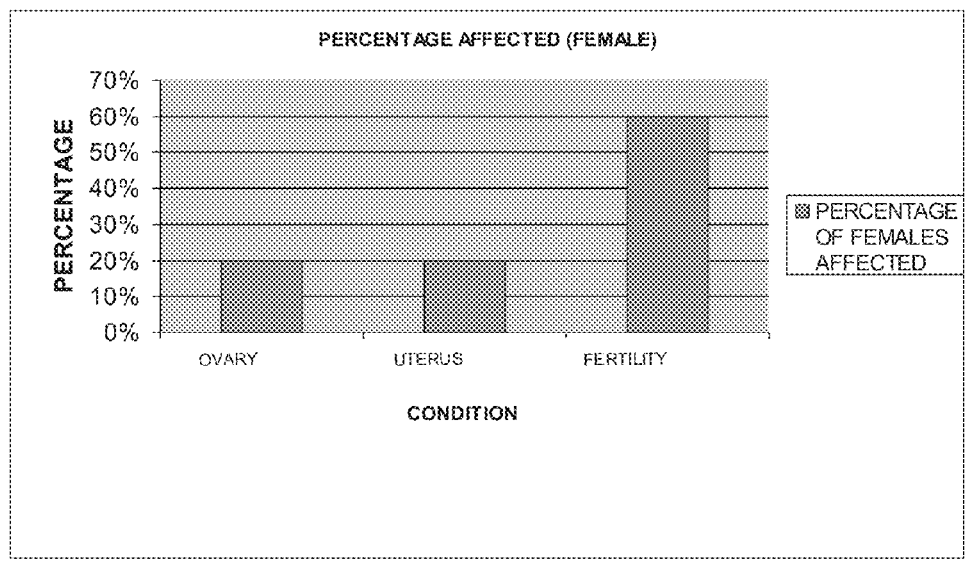
FIG. 5 reports the percentage of female Wistar rats affected for each of the trial parameters indicated: ovaries, uterus and fertility, according to the toxicity study described in Example 2, for animal Groups 1, 2, 3 and 4.

The design and development of the vaccine began with preclinical studies in experimental animals, Wistar rats and some other smaller rodents, where tests were conducted for vaccine toxicity (safety) and effectiveness against certain human tumor types recreated or reproduced in animals.

Some cytotoxicity studies in healthy human lymphocytes were also conducted to test the safety of the vaccine according to the dose applied.

First, a prototype viral protein was sought which would not be harmful to man, and which itself would be capable of stimulating the production of proteins called interferons (alpha, beta and gamma IFN). Second, amino acids were sought to specifically block tumor cells without harming normal cells, so that these tumor cells reach apoptosis. The studies carried out have allowed the observation of tumor regression and metastasis blocking in some cancer types and stages, which corroborates the effectiveness and safety of the vaccine on a human level.

The essential components of the vaccine in the disclosure are:

1. An active component called tumor-associated antigen (ATA) which is present in the serum of patients diagnosed with cancer in a 70 to 90% concentration.

2. An attenuated viral protein, a parvovirus vaccine preparation, which does no harm to humans, but serves to stimulate alpha and gamma IFNs. It is intended to block tumor cell DNA and produce new proteins able to reactivate the T lymphocytes so they learn to recognize and attack tumor cells only, respecting the healthy cells of the cancer patient.

3. The other components correspond to some amino acids which form the primary structure of collagen and serve either to regenerate the collagen lost by action of the tumor cells, or to inhibit the collagenase enzyme, responsible for dissolving the collagen and producing metastatis.

Possible Action Mechanism of the Vaccine:

A possible mechanism of action of the vaccine is the reactivation of the immune system from dendritic cells found in the skin (site of the vaccine application) and which are considered Antigen Presenting Cells (APCs). These cells will stimulate Th1 lymphocytes activating bone marrow cell production of red and white cells and some cytokines such as IL-2, TNF, and INF among others, and inhibiting, through Th2s, other factors such as IL-6 and IL-10. By the action of this stimulus and through the major histocompatibility complex (MHC) of type II, a message is sent through the T helper lymphocytes (Th) and the cytotoxic T lymphocytes (CTL) so that they are able not only to identify the peptide given, but also induce tumor cell apoptosis. Similarly, by presenting the antigen (Ag) associated with the tumor, new antibodies will be produced by action of the B lymphocytes, responsible for provoking a humoral response. It is known that a vaccine is a substance capable of eliciting an immune response. Similarly, an autologous vaccine corresponds to a vaccine prepared from components of the same organism to be treated According to the above, we have that the vaccine components specifically comprise 1. A solvent, particularly distilled water ($H_2O$).

2. An active component: a tumor-associated antigen (ATA), for each type of cancer, corresponding specifically to the antigens Ca 15-3, Ca 125, ACE, Ca 19-9, PSA and alpha fetoprotein.

3. An attenuated DNA virus, of the parvovirus type from a vaccine preparation. The PVC-2 is a virus with DNA containing genes to direct the production of 4 or 5 proteins three of which form the viral capsid. These viruses have only about 5000 nucleotides so sequencing is easy, therefore it is possible to map nucleotides, according to the knowledge of a person of ordinary skill in the art. The virus cannot be transmitted to humans or other animals.

4. Amino acids (AA) essential ones such as lysine and non-essential, among which are proline and glycine.

Method of Preparation

According to the above description the method of obtaining the vaccine comprises the following steps:
1. Get the tumor-associated antigen: from a treatment performed on the cancer patient's blood, which includes coagulation, centrifuging, washing, extraction and filtration of the suspension obtained it is possible to obtain the tumor-associated antigen, depending on the patient's type of cancer.
2. Obtain a vaccine with attenuated DNA virus: the virus used for the preparation of the vaccine of the present disclosure is part of the picornavirus family, called Parvovirus (Latin: parvulos: small and viridae: virus).
3. Place distilled and deionized water in a vessel with magnetic stirrer.
4. Centrifuge.
5. Add, one by one or at the same time, the essential and nonessential amino acids to the distilled water in the desired quantities.
6. Add the viral vaccine preparation
7. Add the tumor-associated antigen
8. Strain and refrigerate.

It should be mentioned that each of these steps can be carried out by a person of ordinary skill in the art, based on their knowledge and according to the examples presented below.

EXAMPLES

The following examples illustrate the present disclosure. However it should be understood that these are not to be interpreted as limitations, in accordance with the knowledge of one of ordinary skill in the art.

Example 1

Preparation of Vaccine

Obtaining Tumor-Associated Antigen

The blood of cancer patients is treated, as follows:

a. Four milliliters of peripheral blood are extracted from the patient in a yellow cap tube containing a blood cell separator gel and left for 1 hour for blood clotting.

b. It is then centrifuged at 2000 rpm for 15 minutes to separate blood cells from the serum and 1 milliliter of the serum is extracted bottling it in an Ependorf tube; then brought to the refrigerator (not freezer) at −4° C. for 3 days.

c. Washing of the serum is then performed with distilled water, centrifuging again at 2000 rpm for 15 minutes, three times.

d. The supernatant, containing the most protein, is suspended in the solution and 0.2 microliters are removed from the suspension with a 5 microliter-micropipette.

e. Finally, filtration is performed with a 0.22 micron millipore filter to eliminate any impurity in the serum f. Once filtered it is necessary that the serum obtained is packaged in an Ependorf tube for later preparation of the autologous vaccine for each patient according to their type of cancer.

It should be noted that a part of that centrifuged, washed and filtered blood serum is sent to blood chemistry analysis to quantify the protein and thereby know the level of antigen in the cooled sample.

Preparation of Attenuated Virus DNA

As indicated above, the virus used in the vaccine in the present disclosure makes part of the picornavirus family, called Parvovirus (Latin: parvulos: small and viridae: virus).

The virus is purchased commercially as a vaccine preparation, containing the live attenuated patented vaccine strain C 154. This highly immunogenic strain has an elevated degree of parvovirus antigen, which has the advantages of a strong response by B and T lymphocytes.

Once the parvovirus vaccine preparation (PVC) has been acquired, prior asepsis and antisepsis, 0.20 ml of said vaccine are extracted with a 100-microliter micropipette, to be added to the 100 milliliters of distilled and deionized water solution located in a container, with the magnetic stirrer dissolving the other components. Apply 0.20 ml of the vaccine preparation so it dissolves in the solution, during the 1 hour the process lasts. Then comes filtering said solution with a 0.22 micrometer millipore type filter to eliminate any residue remaining in the solution; this process is done twice to ensure purity of the preparation and product quality.

Vaccine Preparation

1. Take 100 milliliters of distilled and deionized water in a 200 ml vessel and place a magnetic stirrer to centrifuge at 500 rpm all the components to be added in the preparation of the vaccine.

2. Meanwhile, the three amino acids are taken, one essential and two nonessential one at a time, to the analytical balance as follows: the first amino acid is the nonessential glycine and between 500 and 700 milligrams are taken; the second is the essential amino acid lysine and between 250 and 500 milligrams of this component are taken; the third amino acid is the unessential proline and between 250 and 350 mg are taken; preferably 700 mg of glycine, 400 mg of lysine and 300 mg of proline.

These are added one by one to the distilled water that is centrifuging or one can mix them all together until there is a complete solution so the solutes are dissolved in the solvent. This solution is left centrifuging for at least an hour, until the solution is homogeneous.

Once the three amino acids have been blended, between 200 and 300 microliters (0.2 to 0.3 ml) of the attenuated viral vaccine preparation called PVC-2 (viral protein) are applied, preferably 0.2 milliliters.

3. Once the three amino acids have been blended, between 200 and 300 microliters (0.2 to 0.3 ml) of the attenuated viral vaccine preparation called PVC-2 (viral protein) are applied, preferably 0.2 milliliters.

4. Finally, the tumor-associated antigen is added, which is extracted from the serum of the cancer patient: said antigen has been shown to be circulating at 70 to 90% in peripheral blood. Between 0.1 and 0.3 milliliters of said antigen are taken, preferably 0.2 milliliters according to the specific type of cancer, causing each vaccine to be called autologous, i.e., prepared from the same proteins of the patient. Said antigen once extracted is mixed with the solution, allowing the obtainment of a single solution that will serve as the vaccine preparation.

Before packing the vaccine the whole preparation is filtered in order to purify the solution so that no residue remains, and then cooled in the refrigerator at −4 degrees centigrade, resulting in the active autologous vaccine specific for each type of cancer.

Example 2

Toxicity Study of the Vaccine in Preclinical Studies

Analysis and Toxicity Results in the Preclinical in Vivo Study of the Vaccine in Wistar Rats For the in vivo study of toxicity, we took a population of 60 Wistar rats, divided into five groups each with five males, five females, one male control and one female control, as shown in Table 1.

TABLE 1

Distribution of the animals of the experiment of example 1

| Group | Males | Females | Control Male | Control Female | TOTAL |
|---|---|---|---|---|---|
| 1 | 5 | 5 | 1 | 1 | 12 |
| 2 | 5 | 5 | 1 | 1 | 12 |
| 3 | 5 | 5 | 1 | 1 | 12 |
| 4 | 5 | 5 | 1 | 1 | 12 |
| 5 | 5 | 5 | 1 | 1 | 12 |
| TOTAL | 25 | 25 | 5 | 5 | 60 |

In the five groups (12 rats per group, see Table 1) the vaccine safety study was performed for a period of 90 days, varying the dose in each group. For each group the doses were 0.1, 0.2, 0.3, 0.4 and 0.5 ml respectively. Three doses were applied to each experimental animal, one dose every 10 days.

The control group was inoculated with physiological saline (SNN) with the corresponding dose for each group. All animals were certified Wistar rats obtained from the animal facility of the National Institute of Health (NIH).

The characteristics of the experimental animals are:
Condition of the animals: healthy Average weight. 200 grams.
Average age 3 months. Average Height: 20

The analysis and synthesis of data from the in vivo study of toxicity were made using as a tool the percentage rates and daily observation within the biofacility, for periods of 10 hours daily.

Pathology analysis was performed for organ blocks to verify the toxicity of the vaccine. For the analysis of the data 100% is regarded as the normal daily activity of animals in captivity. Shown below are the data analysis and subsequently the data tables and corresponding Figures.

Data Analysis

For the study of vaccine toxicity data were analyzed from the five groups of animals, with the following results:

Groups 1, 2 and 3: In the experimental animals of these groups with doses of 0.1, 0.2 and 0.3 ml, respectively, no changes in physiology were detected (see Tables 2-7).

TABLE 2

Results Group No. 1
(Dose: 0.1 ml)

| ORGANS ANALYZED BY PATHOLOGY | NUMBER OF ANIMALS AFFECTED | |
|---|---|---|
| | MALES | FEMALES |
| BRAIN | 0 | 0 |
| MENINGES | 0 | 0 |
| SENSES | 0 | 0 |
| HEART | 0 | 0 |
| LUNGS | 0 | 0 |
| KIDNEYS | 0 | 0 |
| LIVER | 0 | 0 |
| PANCREAS | 0 | 0 |
| STOMACH | 0 | 0 |
| INTESTINE | 0 | 0 |
| SEXUAL ORGAN | 0 | 0 |

TABLE 3

Observations on Other Aspects for Group No. 1

| OTHER ASPECTS | COMMENTS | |
|---|---|---|
| | MALES | FEMALES |
| WEIGHT | AVERAGE INCREASE IN EACH ONE 30 grams | AVERAGE INCREASE IN EACH ONE 20 grams |
| SIZE | AVERAGE INCREASE IN EACH ONE 1 cm | AVERAGE INCREASE IN EACH ONE 2 cm |
| COAT | REMAINED NORMAL | REMAINED NORMAL |
| APPETITE | REMAINED NORMAL | REMAINED NORMAL |
| SEXUALITY | REMAINED NORMAL | REMAINED NORMAL |
| WATER CONSUMPTION | REMAINED NORMAL 70 ml per day | REMAINED NORMAL 70 ml per day |
| INFERTILITY | NOT OBSERVED | NOT OBSERVED |
| DEATH | NOT OBSERVED | NOT OBSERVED |

TABLE 4

Results Group No. 2
(Dose: 0.2 ml)

| ORGANS ANALYZED BY | NUMBER OF ANIMALS | |
|---|---|---|
| | MALES | FEMALES |
| BRAIN | 0 | 0 |
| MENINGES | 0 | 0 |
| SENSES | 0 | 0 |
| HEART | 0 | 0 |
| LUNGS | 0 | 0 |

TABLE 4-continued

Results Group No. 2
(Dose: 0.2 ml)

| ORGANS ANALYZED BY | NUMBER OF ANIMALS | |
|---|---|---|
| | MALES | FEMALES |
| KIDNEYS | 0 | 0 |
| LIVER | 0 | 0 |
| PANCREAS | 0 | 0 |
| STOMACH | 0 | 0 |
| INTESTINE | 0 | 0 |
| SEXUAL ORGAN | 0 | 0 |

TABLE 5

Observations on Other Aspects for Group No. 2

| OTHER ASPECTS | COMMENTS | |
|---|---|---|
| | MALES | FEMALES |
| WEIGHT | INCREASE IN AVERAGE WEIGHT 32 gr EACH | INCREASE IN AVERAGE WEIGHT 22 gr EACH |
| SIZE | AVERAGE INCREASE 2 CM IN EACH | AVERAGE INCREASE 2 CM IN EACH |
| COAT | REMAINED NORMAL | REMAINED NORMAL |
| APPETITE | REMAINED NORMAL | REMAINED NORMAL |
| SEXUALITY | REMAINED NORMAL | REMAINED NORMAL |
| WATER CONSUMPTION | REMAINED NORMAL 70 ml per day | REMAINED NORMAL 70 ml per day |
| INFERTILITY | NOT OBSERVED | NOT OBSERVED |
| DEATH | NOT OBSERVED | NOT OBSERVED |

TABLE 6

Results Group No. 3
(Dose: 0.3 ml)

| ORGANS ANALYZED BY PATHOLOGY | RESULST | |
|---|---|---|
| | MALES | FEMALES |
| BRAIN | 0 | 0 |
| MENINGES | 0 | 0 |
| SENSES | 0 | 0 |
| HEART | 0 | 0 |
| LUNGS | 0 | 0 |
| KIDNEYS | 0 | 0 |
| LIVER | 0 | 0 |
| PANCREAS | 0 | 0 |
| STOMACH | 0 | 0 |
| INTESTINE | 0 | 0 |
| SEXUAL ORGAN | 0 | 0 |

TABLE 7

Observations on Other Aspects for Group No. 3

| OTHER ASPECTS | COMMENTS | |
|---|---|---|
| | MALES | FEMALES |
| WEIGHT | AVERAGE INCREASE IN WEIGHT IN EACH 31 gr | AVERAGE INCREASE IN WEIGHT IN EACH 20 gr |
| SIZE | AVERAGE SIZE INCREASE IN EACH 1.5 cm | AVERAGE SIZE INCREASE IN EACH 2 cm |
| COAT | REMAINED NORMAL | REMAINED NORMAL |
| APPETITE | REMAINED NORMAL | REMAINED NORMAL |
| SEXUALITY | REMAINED NORMAL | REMAINED NORMAL |
| WATER CONSUMPTION | REMAINED NORMAL 70 ml per day | REMAINED NORMAL 70 ml per day |
| INFERTILITY | NOT OBSERVED | NOT OBSERVED |
| DEATH | NOT OBSERVED | NOT OBSERVED |

Group 4: In the experimental animals in group 4 (0.4 ml dose), according to information obtained by daily observation and taking into account that the normal state of the animal's sexual behavior is five copulations, a decrease in sexual activity was noted, their number of copulas being reduced to one. (5 copulas are taken as 100%).

Sixty percent of males presented conditioned erectile dysfunction. In areas such as appetite (food intake) this decreased to 85%, water consumption decreased to 72% and sexuality decreased to 15%. In females, aspects such as appetite, water consumption and sexual activity were also affected as for the group of males. For the above results, see Tables 8-11 and FIGS. 1-5.

TABLE 8

Results Group No. 4
(Dose: 0.4 ml)

| ORGANS | RESULTS | |
|---|---|---|
| ANALYZED BY PATHOLOGY | AFFECTED MALES | AFFECTED FEMALES |
| BRAIN | 0 | 0 |
| MENINGES | 0 | 0 |
| SENSES | 0 | 0 |
| HEART | 0 | 0 |
| LUNGS | 0 | 0 |
| KIDNEYS | 0 | 0 |
| LIVER | 0 | 0 |
| PANCREAS | 0 | 0 |
| STOMACH | 0 | 0 |
| INTESTINE | 0 | 0 |
| TESTICLE | 3 | — |
| OVARY | — | 1 |
| UTERUS | — | 1 |
| TOTAL | 3 | 2 |

TABLE 9

Observations on Other Aspects for Group No. 4

| | COMMENTS | | NUMBER OF | |
|---|---|---|---|---|
| OTHER ASPECTS | MALES | FEMALES | MALES | FEMALES |
| WEIGHT | NO INCREASE | NO INCREASE | 0 | 0 |
| SIZE | NO INCREASE | NO INCREASE | 0 | 0 |
| COAT | NORMAL | NORMAL | 0 | 0 |
| APPETITE | DECREASED BY 15% | DECREASED BY 15% | 0 | 0 |
| SEXUALITY | DECREASED BY 85% | DECREASED BY 85% | 0 | 0 |
| WATER | DECREASED BY 20 | DECREASED BY 20 | 0 | 0 |
| STERILITY | WAS OBSERVED | WAS OBSERVED | 2 | 3 |
| DEATH | NOT OBSERVED | NOT OBSERVED | 0 | 0 |
| TERATOGENESIS | | NOT OBSERVED | 0 | 0 |

PERCENTAGE OF MALES AFFECTED The reference value of 100% is five experimental animals.

TABLE 10

| ASPECT | BEFORE | AFTER |
|---|---|---|
| APPETITE | 100% | 85% |
| SEXUALITY | 100% | 15% |
| WATER TAKEN | 100% | 72% |
| AFFLICTION | | % |
| TESTICLES | | 60% |
| STERILITY | | 40% |

PERCENTAGE OF FEMALES AFFECTEDD The reference value of 100% is five experimental animals

TABLE 11

| ASPECT | BEFORE | AFTER |
|---|---|---|
| APPETITE | 100% | 85% |
| SEXUALITY | 100% | 15% |
| WATER | 100% | 72% |
| AFFLICTION | | % |
| OVARY | | 20% |
| UTERUS | | 20% |
| FERTILITY | | 60% |

Group 5: In this group of animals, inoculated with doses of 0.5 milliliters, according to information obtained by daily observation and taking into account that the normal state of the animal's sexual behavior is five copulations, a decrease in sexual activity was noted, their the number of copulas being reduced.

Figure 6:
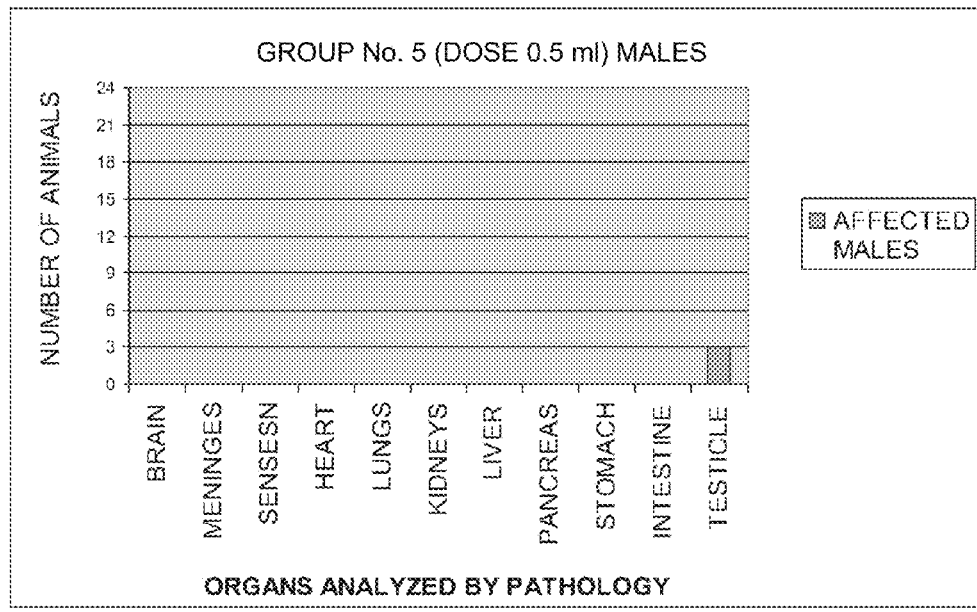
FIG. 6 reports the quantity of male Wistar rats affected in the testicles, according to the toxicity study described in Example 2, for animal Group 5.
Figure 7:
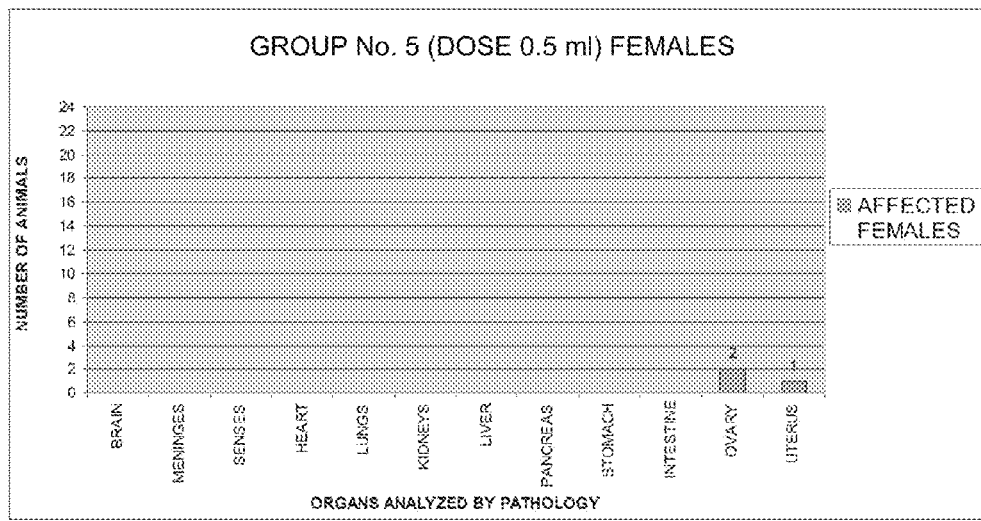
FIG. 7 reports the percentage of female Wistar rats affected for each of the trial parameters indicated: ovaries and uterus, according to the toxicity study described in Example 2, for animal Group 5.
Figure 8:
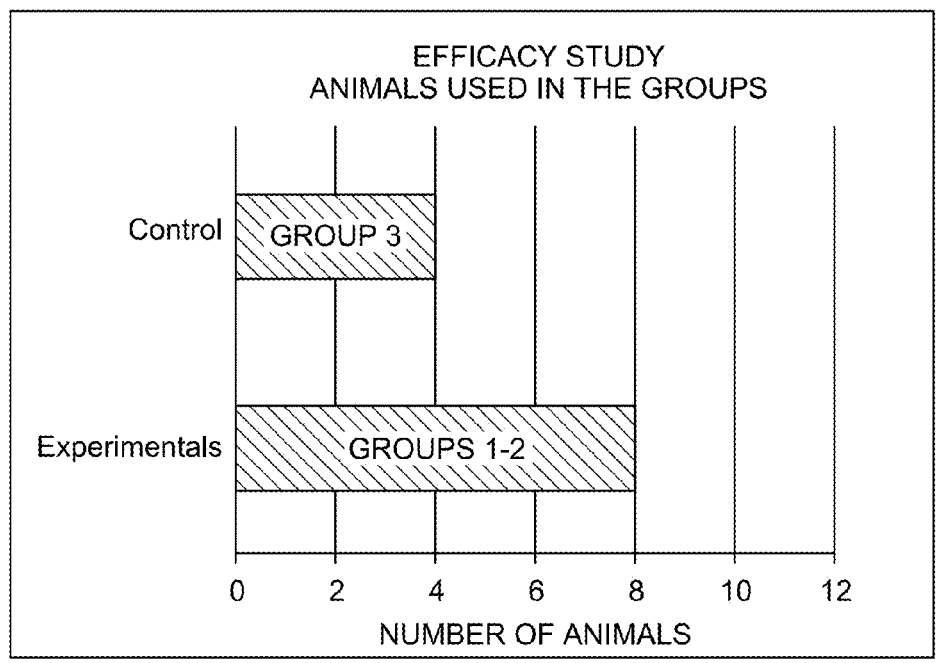
FIG. 8 shows the number of animals (Wistar rats) used in the effectiveness study, according to Example 3, regarding the control and animal Groups 1 and 2.
Figure 9:
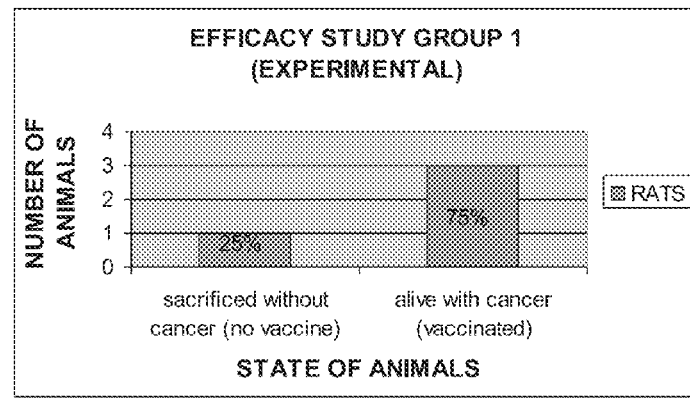
FIG. 9 reports the percentage of living animals with cancer that were vaccinated and the percentage of animals sacrificed for Experimental Group 1, according to the effectiveness study of Example 3.
Figure 10:
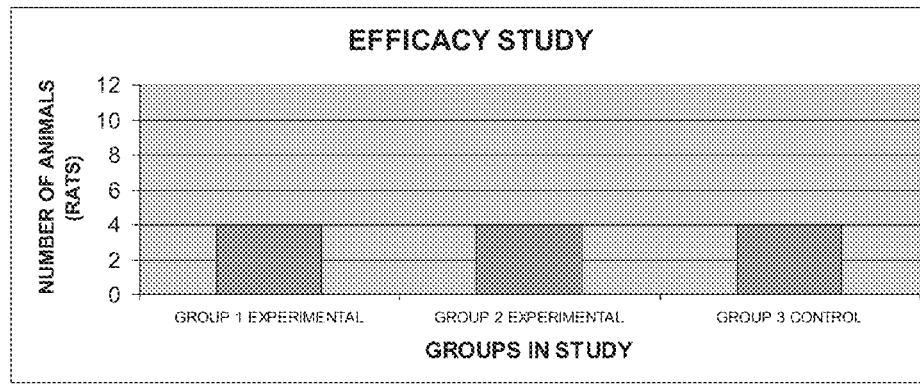
FIG. 10 indicates the number of animals (Wistar rats) in each of the experimental groups, according to the effectiveness study in Group 3.
Figure 11:
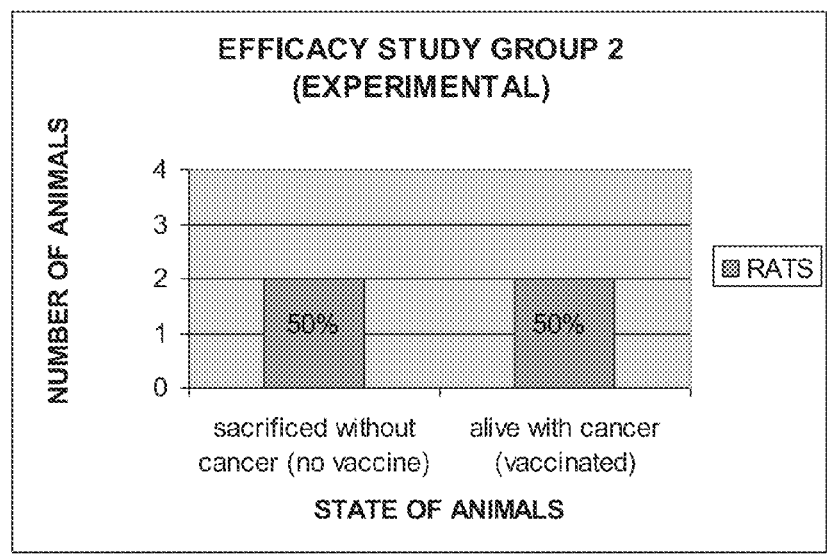
FIG. 11 reports the percentage of living animals with cancer that were vaccinated and the percentage of animals sacrificed for Experimental Group 2, according to the effectiveness study in Example 3.
Figure 12:
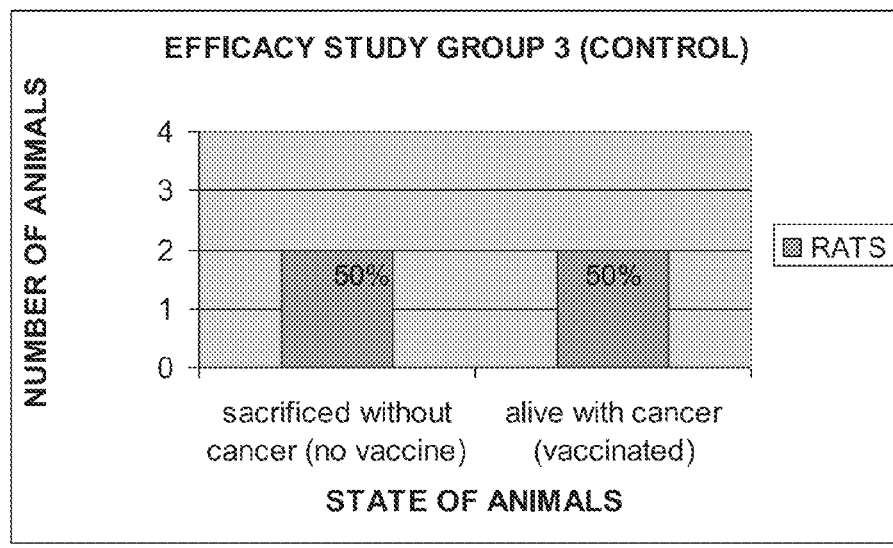
FIG. 12 reports the number of living animals with cancer that were vaccinated and the percentage of animals sacrificed for Experimental Group 3, according to the effectiveness study in Example 3.
Figure 13:
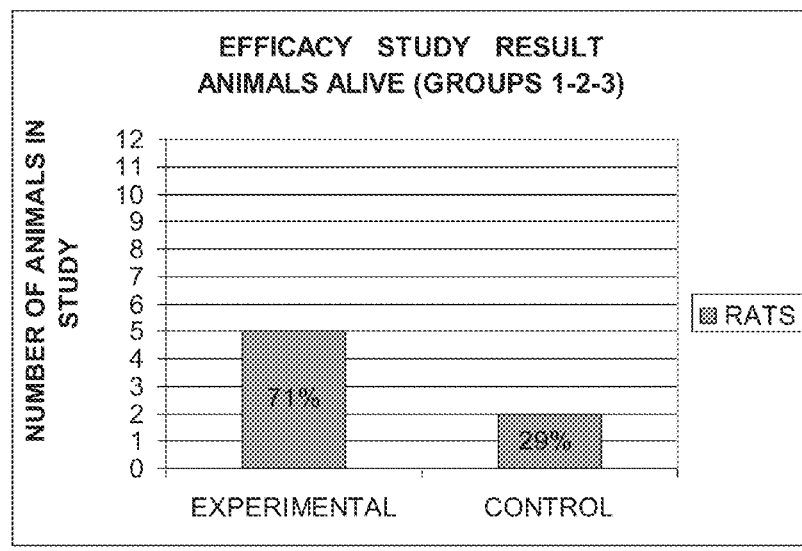
FIG. 13 indicates the percentage of total living animals, adding the Experimental Groups 1, 2 and 3 and the percentage of living control animals, according the effectiveness study in Example 3.
Figure 14:
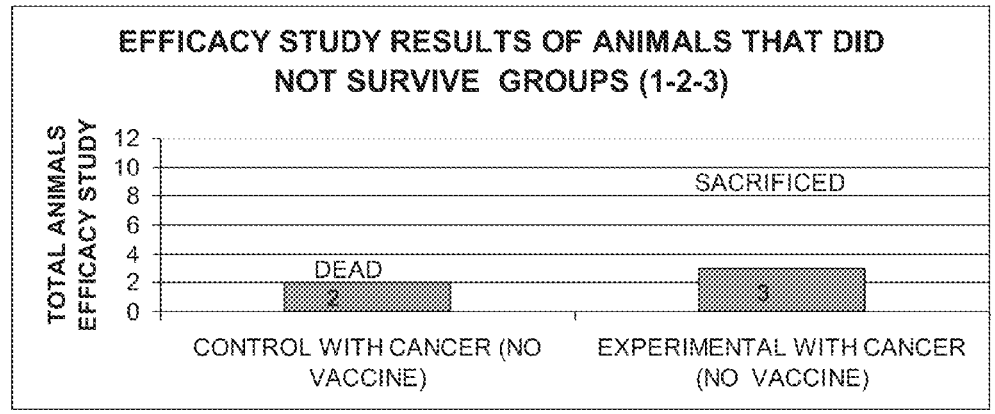
FIG. 14 indicates the total number of animals sacrificed, adding Experimental Groups 1, 2 and 3 and the percentage of control animals sacrificed, according to the effectiveness study in Example 3.
Figure 15:
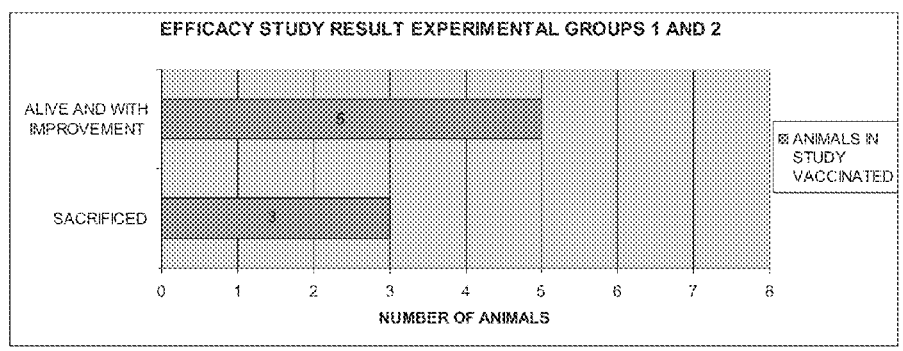
FIG. 15 reports the number of living animals with improvement and those sacrificed for Experimental Groups 1 and 2, according to the effectiveness study in Example 3.
Figure 16:
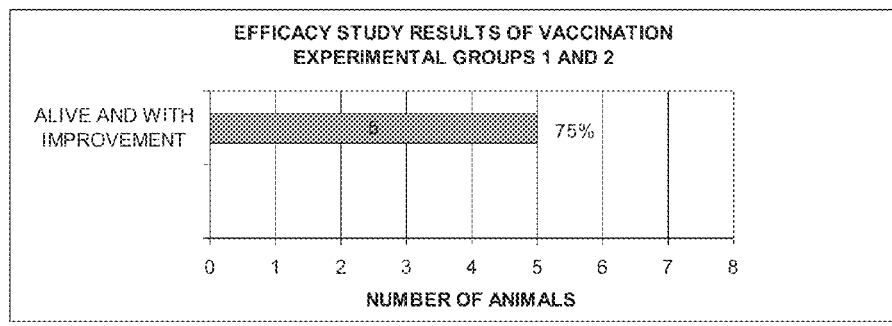
FIG. 16 shows the percentage of living animals with improvement, according to FIG. 15, for Experimental Groups 1 and 2, according to the effectiveness study in Example 3.
Figure 17:
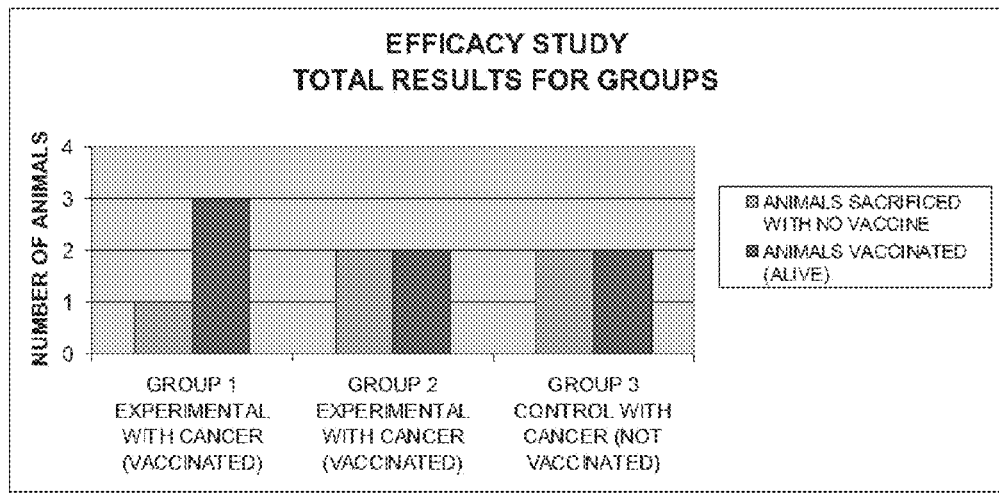
FIG. 17 compares the number of living and sacrificed animals, with or without vaccination, for Experimental Groups 1 and 2, according to the effectiveness study in Example 3.

In areas such as appetite, this dropped to 80%, water consumption decreased to 57% and sexuality decreased to 10%. In females of this group, pathophysiological changes were seen in ovaries by 40%, decreased uterine function (procreation) by 20% and fertility was affected. In females, aspects such as appetite, water consumption and sexual activity were also affected as for the group of males. According to the above, it is shown that doses greater than 0.3 milliliters exhibit alterations in the reproductive organs of both males and females and variation in the normal behavior of the animal, such as food consumption, water and reproductive activity. For the above results, see Table 12 and FIGS. 6 and 7

TABLE 12

Results Group No. 5
(dose 0.5 ml)

| ORGANS | RESULTS | |
|---|---|---|
| ANALYZED BY PATHOLOGY | MALES AFFECTED | FEMALES AFFECTTED |
| BRAIN | 0 | 0 |
| MENINGES | 0 | 0 |
| SENSES | 0 | 0 |
| HEART | 0 | 0 |
| LUNGS | 0 | 0 |

TABLE 12-continued

| Results Group No. 5 (dose 0.5 ml) | | |
|---|---|---|
| ORGANS ANALYZED BY PATHOLOGY | RESULTS MALES AFFECTED | FEMALES AFFECTTED |
| KIDNEYS | 0 | 0 |
| LIVER | 0 | 0 |
| PANCREAS | 0 | 0 |
| STOMACH | 0 | 0 |
| INTESTINE | 0 | 0 |
| TESTICLES | 3 | 0 |
| OVARY | 0 | 2 |
| UTERUS | 0 | 1 |
| TOTAL | 3 | 3 |

Example 3

Study of Effectiveness in Preclinical in Vivo Study of the Vaccine in Wistar Rats Some solid solid (carcinomas) and hematopoietic (leukemias and lymphomas) tumors were induced from human cancer cells (xenotransplantation) in rats, confirming that the rats treated at a dose of 0.2 ml showed tumor regression, which gives an indication of the potential effectiveness of the vaccine in some of the induced tumors resulting in survival and quality of life in the treated animals.

The study consisted of three groups of Wistar rats, each consisting of two females and two males, two of these groups called experimental and one a control group. The study was conducted in 12 rats, 6 females and 6 males, mean age 2 to 3 months, with an average weight of 50 to 60 grams and an average size between 20 and 25 cm; all animals were healthy and well fed at baseline (see Tables 13 and 14).

TABLE 13

| GROUP 1: EXPERIMENTAL | GROUP 2: EXPERIMENTAL | GROUP 3: CONTROL |
|---|---|---|
| 2 MALES 2 FEMALES | 2 MALES 2 FEMALES | 2 MALES 2 FEMALES |

TABLE 14

| GROUP 1 | GROUP 2 | GROUP 3 |
|---|---|---|
| Leukemia: 0.2 ml × 3 doses | Leukemia: 0.2 ml × 3 doses | Leukemia: 0.2 ml × 3 doses |
| Lymphoma: 0.2 ml × 3 dosis | Lymphoma: 0.2 ml × 3 dosis | Lymphoma: 0.2 ml × 3 dosis |
| Uterus Carcinoma: 0.2 ml × 3 dosis | Uterus Carcinoma: 0.2 ml × 3 dosis | Uterus Carcinoma: 0.2 ml × 3 dosis |

Three doses of tumor cells were applied at lower limb levels to each animal intramuscularly (IM), with an interval of 10 days between each dose. After daily observation for 6 weeks, 3 rats were sacrificed, two males and one female in the experimental group, sending the organ blocks to pathology to see if cancer had developed, with the following results:
  a. Endometrial hyperplasia, consistent with well-differentiated adenocarcinoma.
  b. Lymphoid hyperplasia, low defenses, possibly resulting from leukemia.
  c. Nodal hyperplasia, low defenses.
  d. Lymphoid hyperplasia.
  e. Hyperplastic bone marrow, leukemic phase reaction.
  f. Endometrium with dysplasia changes and areas suggestive of carcinoma.
  g. Lymph nodes with moderate hyperplasia, hyperplastic gastric mucus, colonic lymphoid hyperplasia.

During the time of observation of the animals inoculated with human cancer cells (experimental group and control group), a significant deterioration of these was noted, such as tissue atrophy (cachexia), moderate to severe malnutrition, weight loss, hair loss, asthenia, adynamia and death.

Once the result of the cancer process was confirmed by pathology, Groups 1 and 2, designated experimental, were started on the vaccination scheme with a dose of 0.2 ml of vaccine subcutaneously in three doses with an interval of 10 days between doses. The control rats were administered physiological saline in the same number of doses during the same time. An observation period of 30 to 60 days then began, which showed:
  1. Hair Regeneration.
  2. Improvement of nutritional status.
  3. Improved physical activity.
  4. Decreased tumors.
  5. Improvement in quality of life.
  6. Survival was achieved beyond the stipulated time.
  7. After performing removal of the tumor in some of the animals, necrosis (angiogenesis) and encapsulation was evidenced in the vessels supplying the tumor.

The results obtained with vaccination after tumor cell reproduction in experimental animals showed that:
  1. It is possible to reproduce tumor cells by xenograft.
  2. While not reaching an advanced stage of cancer in the experimental sample, the induction process of the same was demonstrated in animals.
  3. After demonstrating the cancer from the histopathology study, the vaccine acted effectively to block the progression of this disease and inhibiting the early death of the animal.
  4. It was possible to confirm the survival of the animals treated with the vaccine.
  5. It is possible to treat cancer in early stages (I-II).
  6. The vaccine is capable of encapsulating tumors without allowing metastasis.
  7. It is possible to give quality of life and survival to the animals affected by said disease.
  8. Vaccinated rats survived beyond 24 months, normal lifespan of a rat.
  9. The rats improved their nutritional status.
  10. The dead rats (2) were the control rats, which followed the carcinogenic process and for whom no treatment against the disease was started.
  11. Altogether 5 experimental rats survived, 2 males and 3 females. Two males and one female were slaughtered and sent to pathology and 2 control rats died during the study, leaving only two that survived for a longer time, thanks to the nutrition supplied.

12. The effectiveness study allows an inference that the vaccine acts as a stimulus for the reactivation of the immune system affected by cancer and that it is able to block cancer cells (see article, Segura H, "Immunotherapy: Adjuvant in the Treatment of Melanoma," Pilot Study, in *Scientific Threshold* No 7 (December), pgs. 72-76.

13. Finally it was shown that animals with good nutrition could achieve an overall survival.

The representation of the above results can be seen in FIGS. 8 to 17.

The WHO evaluation criteria for the clinical phase study of patients with cancer are:
Improvement
Partial clinical response ≥25% and/or ≥50%
Complete disappearance of the lesions.
Complete clinical response 100%
Stable
Disease progression <=25%
Decline
Progression of disease >25% in the patient and/or appearance of new lesions.

Example 4

Clinical Phases I and II of Cancer Treatment with the Vaccine

After obtaining the results of the preclinical studies, the UMB Ethics Committee approved the clinical study of cancer patients. A prior informed consent allowed recruitment of four case study patients with different types of cancer and in different stages, who voluntarily wanted to be part of the cancer vaccine study. Two of them, a patient with breast cancer in stage III and one patient with ovarian cancer in stage IV, had already been treated with chemotherapy and radiation therapy several times without a favorable response; on the contrary, their overall state deteriorated and the cancer progressed. These two patients were able to obtain quality of life and survival for more than two years. Another patient suffered from skin cancer of stage II melanoma type. Two of his relatives had died months before from the same disease, with complications from chemotherapy and radiotherapy. Therefore, the patient decided to undergo the vaccine application, without using any further treatment. Today, he has completed five asymptomatic years with quality of life, without the cancer having progressed.

Another patient with a pleomorphic sarcoma with high grade malignancy in the left leg had received a suggestion to undergo surgery after starting treatment with the vaccine, since he would not accept conventional treatments. This patient had been declared terminal due to the type of tumor and been given only a month to live. With the vaccine a four-year survival with quality of life was achieved; the tumor then entered into progression, probably because in the last year the patient was persuaded to undergo chemotherapy and radiation, terminating his quality of life and ultimately bringing him to death.

After observing in these patients that the vaccine was safe and effective, it was decided to recruit patients designated as "compassionate," which were approved by the Ethics Committee of the UMB: these were patients who had been given up on by traditional medicine. The vaccine treatment allowed a better quality of life for most of them, from which was noted that the vaccine is more effective in certain types of cancer. Additionally, a longer survival than predicted by traditional medicine was achieved for such cases.

After the above studies and observations, it was decided to initiate a Clinical Phase I and II study recruiting cancer patients in all stages and of all types, to see more clearly in what types of cancer the vaccine worked better. It was observed that in four types of cancer, melanoma skin cancer, breast cancer, prostate cancer and lymphomas, the vaccine showed better results. Therefore, the study points to those four types of cancer and the observation of results in 24 months.

The results of the above studies are illustrated in FIGS. 18 to 44 and Table 15, as detailed below.

Figure 18:
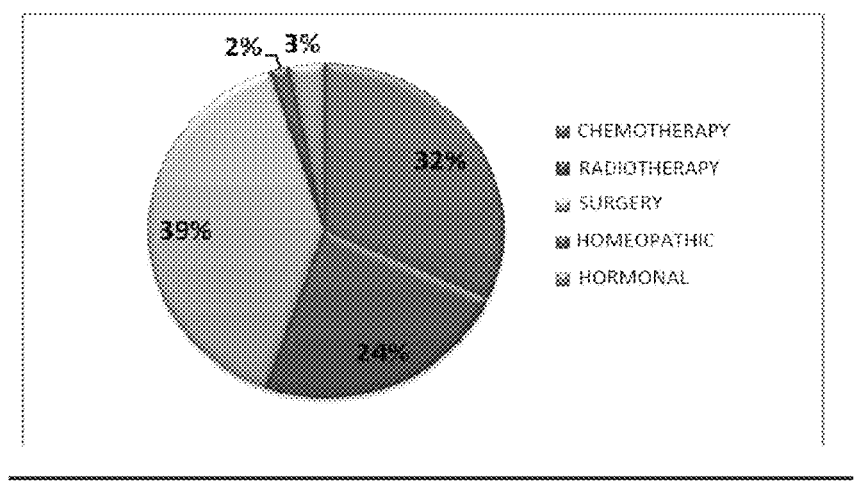
FIG. 18 shows the percentage of patients in clinical phase II who reported some cancer treatment prior to vaccination, according to the study of clinical phases I and II in Example 4.
Figure 19:
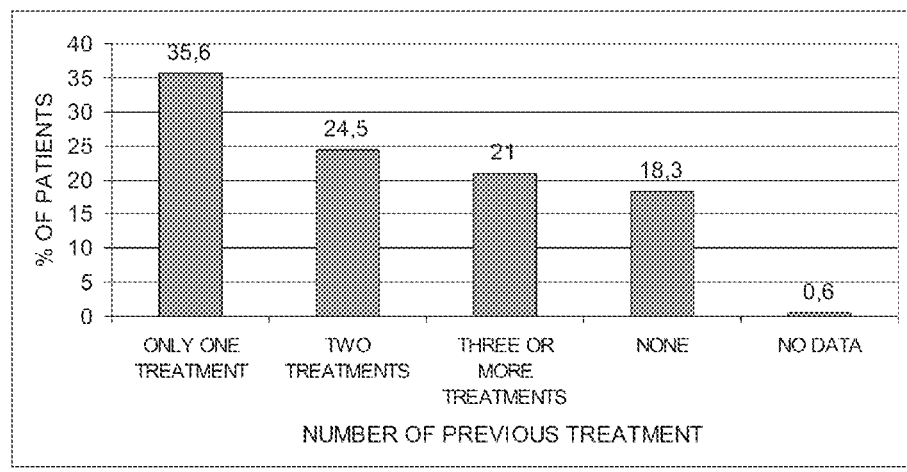
FIG. 19 shows the percentage of patients in clinical phase II who had been submitted to one or more cancer treatments prior to the vaccine, according to the study of clinical phases I and II in Example 4.

FIGS. 18 and 19. Clinical phase II study which shows the percentage of patients who have had treatment previous to the vaccine and the number of treatments prior to the vaccine.

Figure 20:
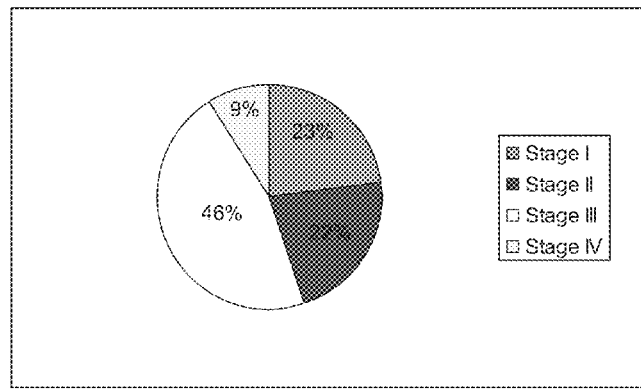
FIG. 20 shows the percentage of patients who were in Stages I, II, III and IV of cancer, according to the study of clinical phases I and II in Example 4.

FIG. 20. The vaccine research study has shown that the greatest number of patients treated are in advanced stages III and IV and metastasis. Hence the importance of the clinical response to the vaccine in patients who have been declared terminal.

Figure 21:
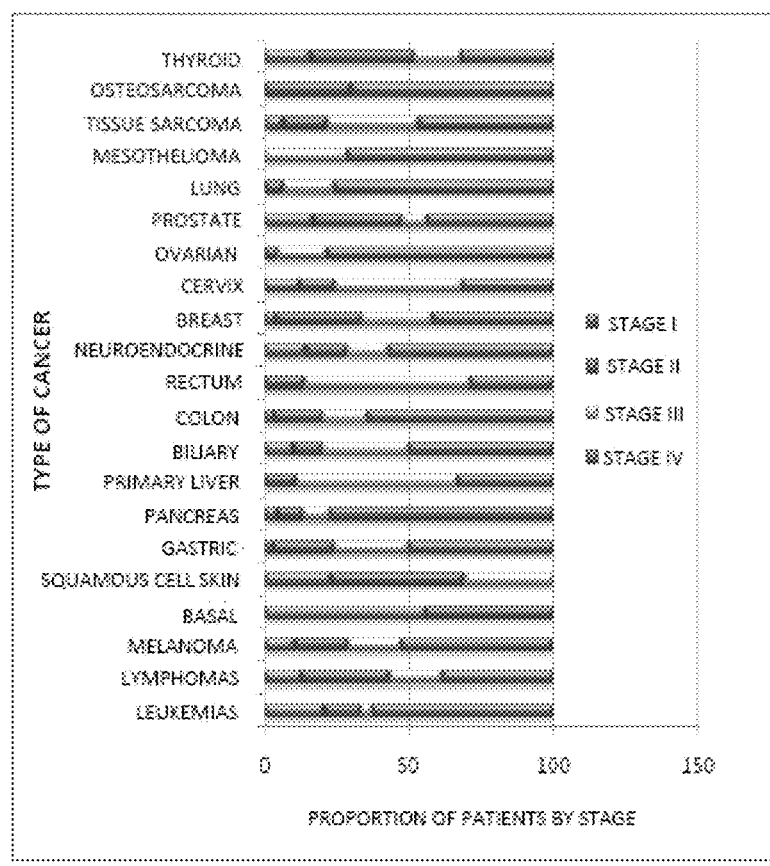
FIG. 21 shows the proportion of patients relative to the type and stage of cancer, according to the study of clinical phases I and II in Example 4.

FIG. 21. The FIG. shows the different types of cancer treated with the vaccine, as well as the stage at which the patients are.

Figure 22:
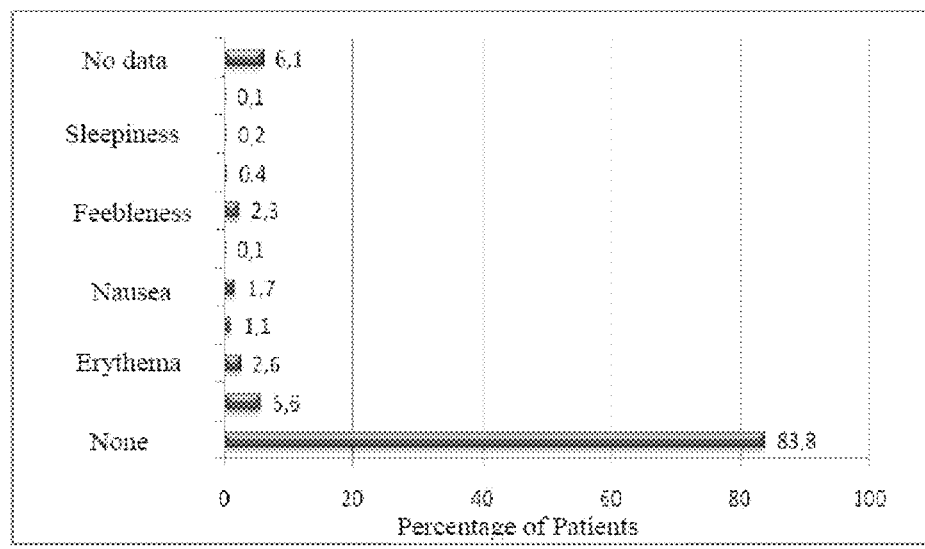
FIG. 22 reports the percentage of patients who displayed side effects to the vaccine, as well as the corresponding side effect, according to the study of clinical phases I and II in Example 4.

FIG. 22. Safety results of the vaccine in vaccinated patients, showing that the side effects observed are considered mild and acute; yet 83% of patients showed no side effects in relation to the small proportion of patients who had some type of reaction. It should be noted that some of the unwanted side effects for patients, such as nausea and despondency, coincide with previous treatments before application of the vaccine. It is noted in the above FIGS that the majority of patients received other treatments, which would imply reevaluating these side effects to the vaccine.

Figure 23:
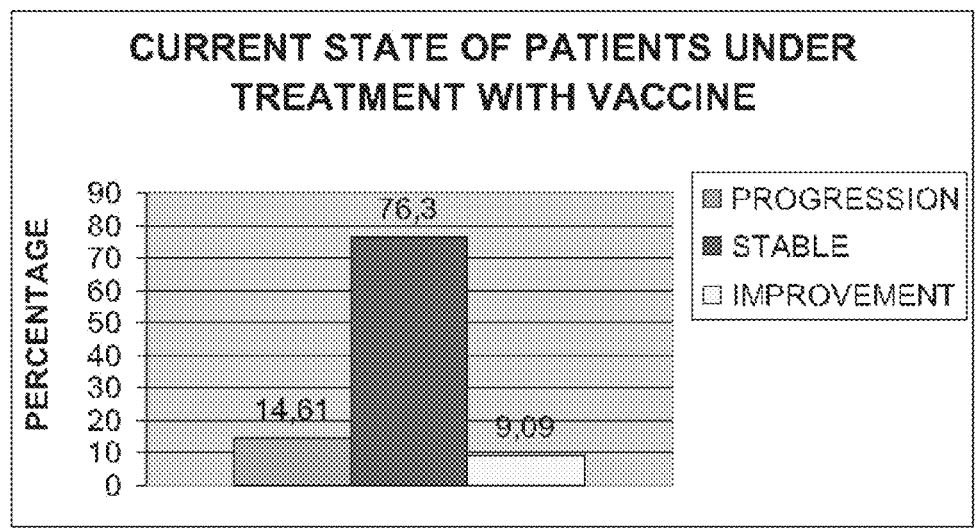
FIG. 23 indicates the current condition of the patients, with the percentage corresponding to: decline, stability, and improvement, according to the study of clinical phases I and II in Example 4.

FIG. 23. The study showed that 76% of patients remained stable, i.e. no progression of disease or their lesions did not increase more than 25% from their initial state during treatment with the vaccine, and that 9% improved, i.e. their tumor lesions decreased or disappeared during treatment, giving them quality of life and survival beyond that predicted by conventional treatments. However 14% continued in progression, i.e. the cancer increased whether due to its advanced stage or because the vaccine was definitely unable to block metastasis Table 15 Comparative study of a CBC of a patient with acute lymphoid leukemia, before and after treatment with the vaccine.

TABLE 15

| Date | Hto | Hb | PML | Lymph | Plt | Leuk |
| --- | --- | --- | --- | --- | --- | --- |
| May 10, 2005 | 31.4 | 10.7 | 31 | 98.7 | 169 | 1.200 |
| May 31, 2005 | 33 | 11.3 | 47 | 46 | 152 | 1.200 |
| Apr. 7, 2004 | 25.2 | 8.7 | 40 | 56 | 125 | 1.200 |
| Mar. 14, 2000 [sic] | 32.5 | 10.7 | 81.7 | 6.9 | 217 | 4.800 |
| Mar. 12, 2007 | 44.4 | 15.2 | 60.1 | 1.6 | 176 | 5.900 |
| Aug. 1, 2007 | 45.3 | 15.5 | 60.4 | 30.3 | 208 | 6.200 |
| Nov. 20, 2007 | 45.6 | 16.1 | 69.6 | 21.4 | 223 | 7.300 |
| Mar. 3, 2008 | 43.4 | 14.8 | 69.4 | 21.8 | 196 | 7.500 |
| Apr. 29, 2008 | 43 | 14.2 | 69.4 | 21.2 | 195 | 6.700 |
| Jul. 9, 2008 | 44.4 | 14.3 | 66 | 28 | 209 | 5.620 |
| Mar. 10, 2009 | 47.7 | 16.1 | 62.9 | 25.6 | 223 | 5.810 |
| Aug. 11, 2009 | 45.6 | 15.1 | 6.6 | 31.9 | 209 | 6.400 |

Figure 24:
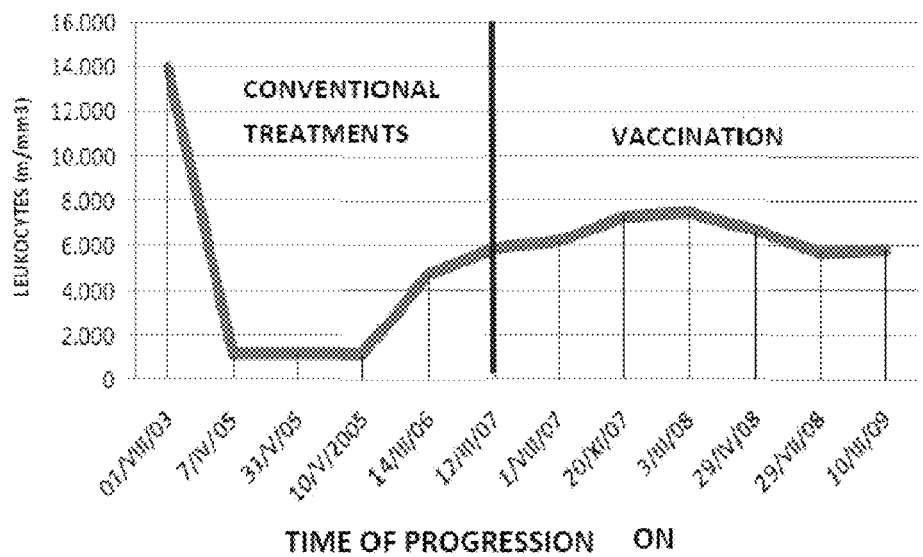
FIG. 24 corresponds to the leukocyte count curve for a patient with acute lymphoid leukemia, after treatment with the vaccine, according to the study of clinical phases I and II in Example 4.
Figure 25:
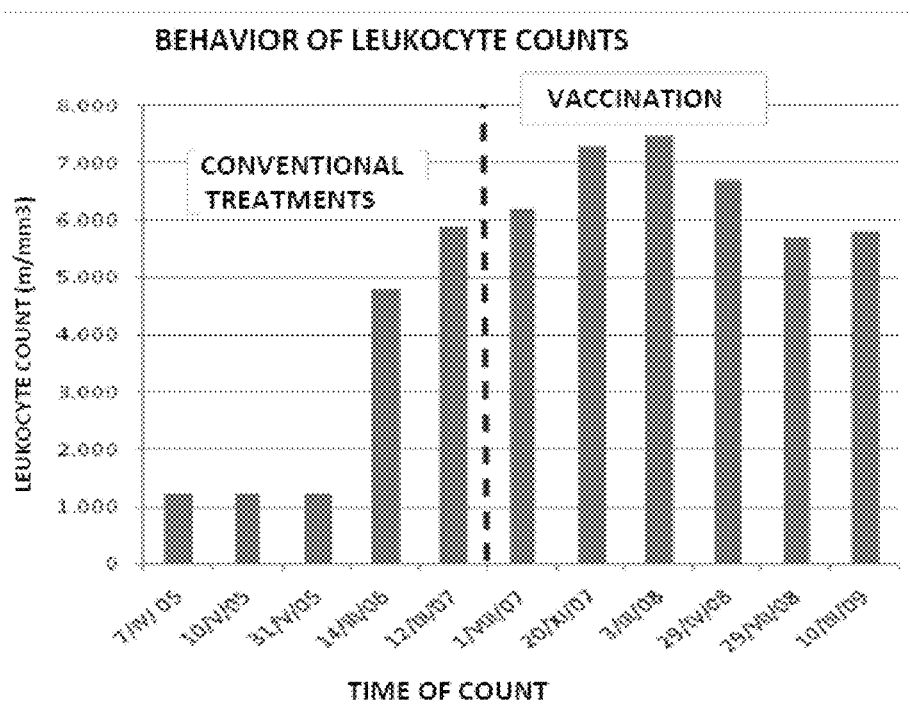
FIG. 25 corresponds to the leukocyte count behavior for the patient with acute lymphoid leukemia, after treatment with the vaccine, according to the study of clinical phases I and II in Example 4.

FIGS. 24 and 25. The sharp decline of leukocytes (leukopenia) is observed after applying chemotherapy, and how it is reactivated and remains normal during vaccination.

Figure 26:
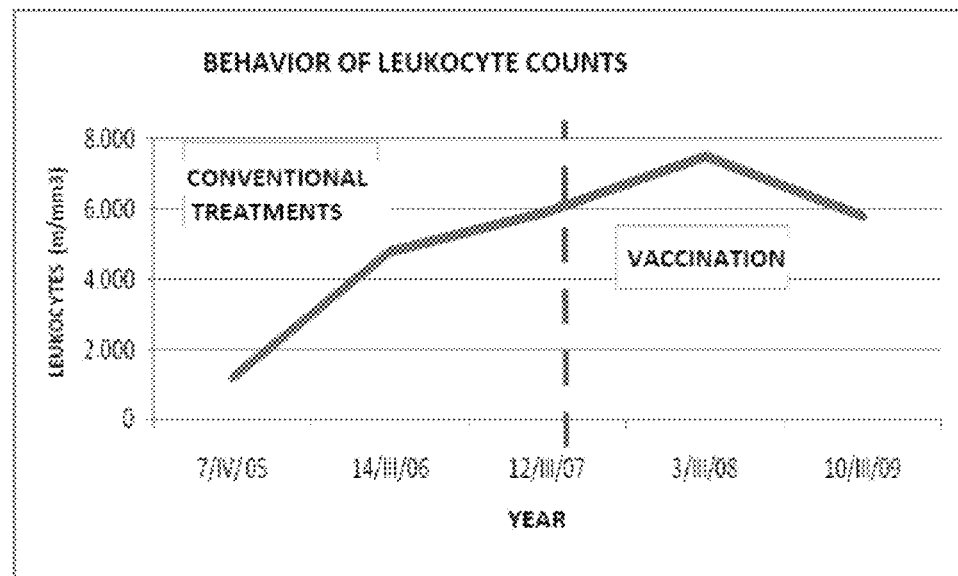
FIG. 26 reports the leukocyte count curve for the patient with acute lymphoid leukemia, after treatment with the vaccine, according to the study of clinical phases I and II in Example 4.

FIG. 26. It can be observed that the leukocytes are maintained at a normal standard, causing bone marrow to remain normally active after vaccination during the 24 months of treatment.

Figure 27:
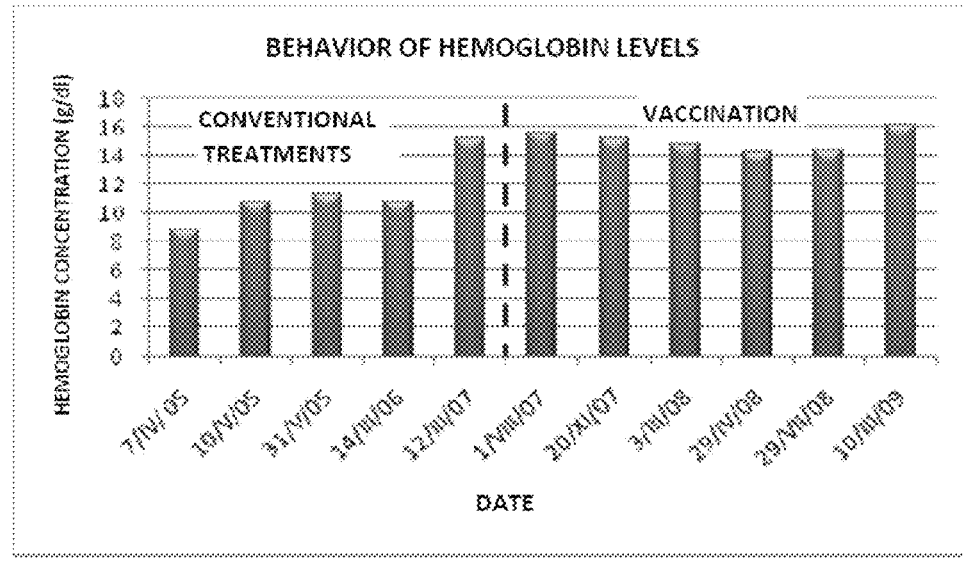
FIG. 27 refers to the behavior of hemoglobin levels for the patient with acute lymphoid leukemia, after treatment with the vaccine, according to the study of clinical phases I and II in Example 4.

FIG. 27. It can be observed that hemoglobin levels for the patient are maintained during treatment with the vaccine, which shows that it activates the bone marrow maturing red and white series cells.

Figure 28:
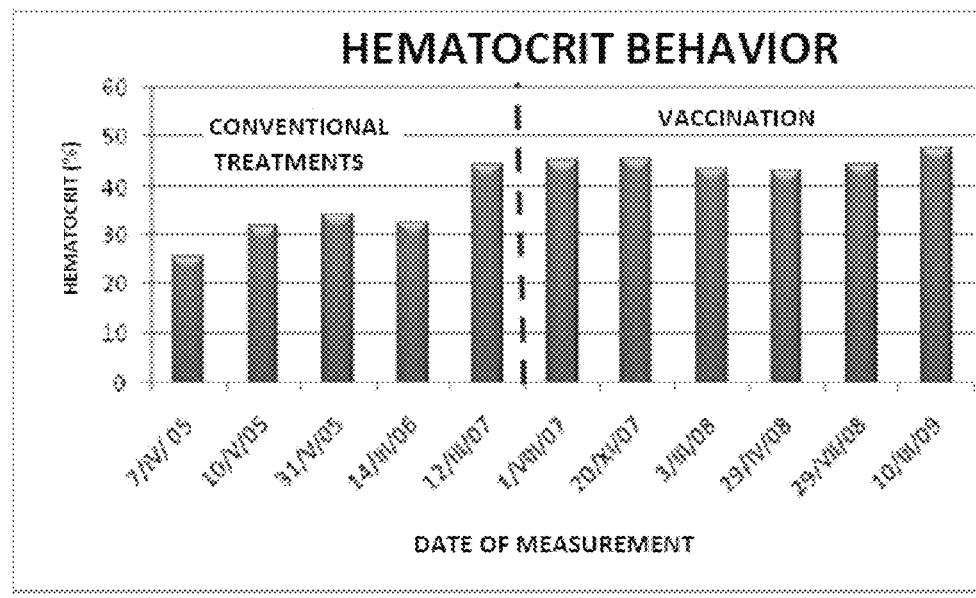
FIG. 28 reports the hematocrit behavior for the patient with acute lymphoid leukemia, after treatment with the vaccine, according to the study of clinical phases I and II in Example 4.
Figure 29:
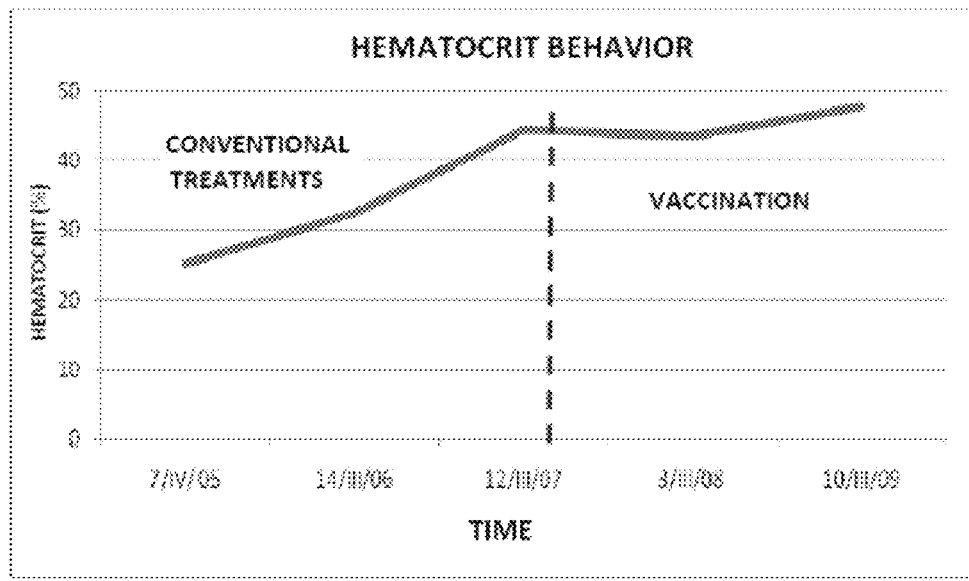
FIG. 29 reports the behavior curve for the hematocrit in the patient with acute lymphoid leukemia, after treatment with the vaccine, according to the study of clinical phases I and II in example 4.

FIGS. 28 and 29. Similarly, the activity of cells of the red series is maintained; they remain mature throughout the treatment time, unlike conventional treatments which lower such blood levels.

Figure 30:
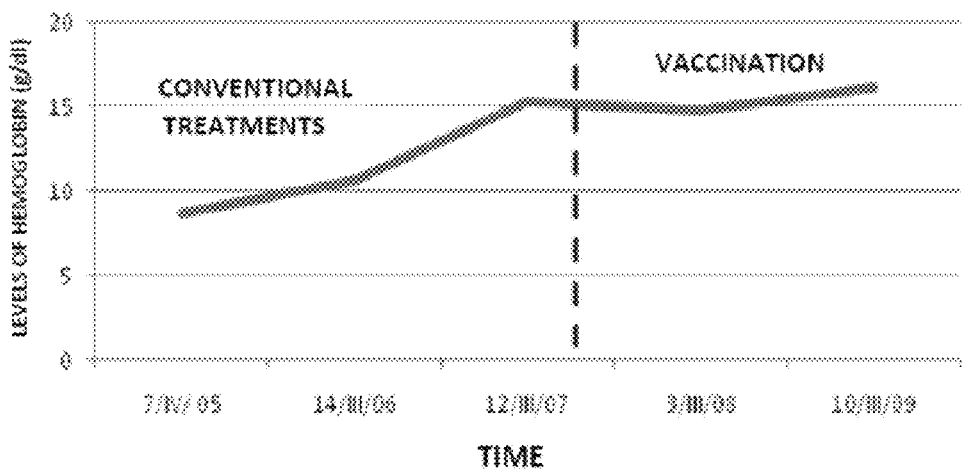
FIG. 30 corresponds to the hemoglobin level curve for patients with acute lymphoid leukemia, after treatment with the vaccine, according to the study of clinical phases I and II is Example 4.

FIG. 30. It can be seen how the vaccine favors blood levels in the bone marrow and produces healthy mature cells.

Figure 31:
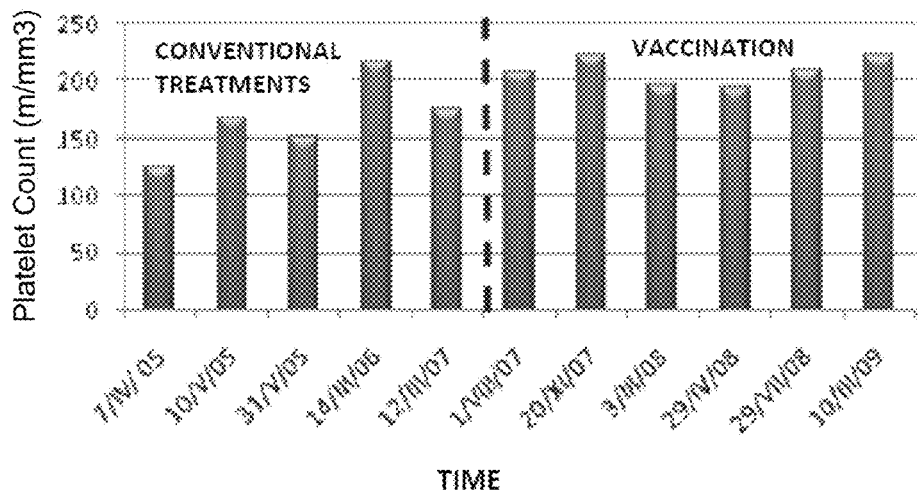
FIG. 31 reports the behavior of the platelet count for the patient with acute lymphoid leukemia, after treatment with the vaccine, according to the study of clinical phases I and II in Example 4.
Figure 32:
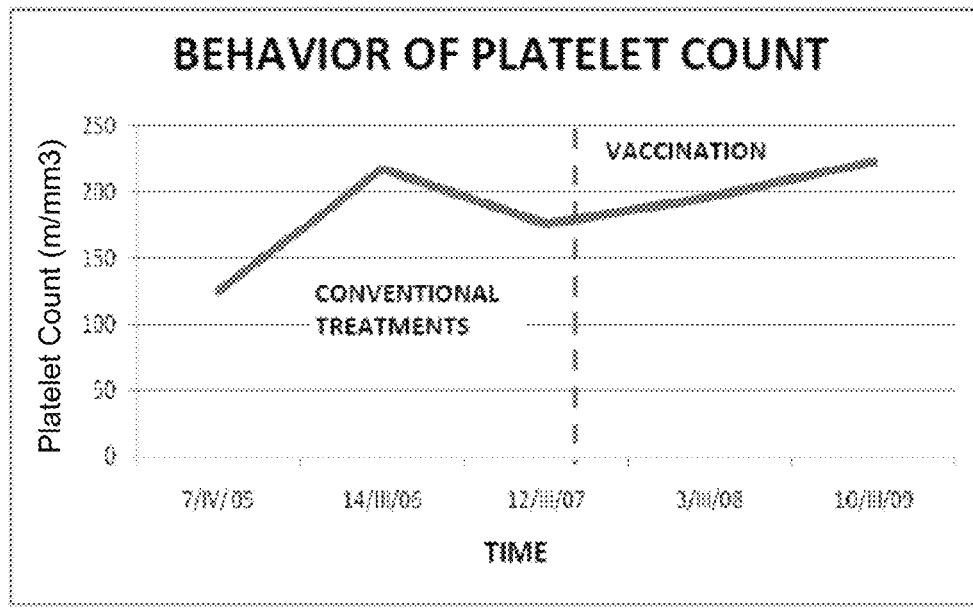
FIG. 32 corresponds to the behavior curve of the platelet count for the patient with acute lymphoid leukemia, after treatment with the vaccine, according to the study of clinical phases I and II in Example 4.

FIGS. 31 and 32. Similarly, we observe that all cells produced in the bone marrow, including platelets, have the same behavior and their number is not altered; on the contrary, blood levels are maintained within the normal range, which implies that the vaccine is not only effective, but also regenerates and maintains the hematopoietic system in the bone marrow.

Figure 33:
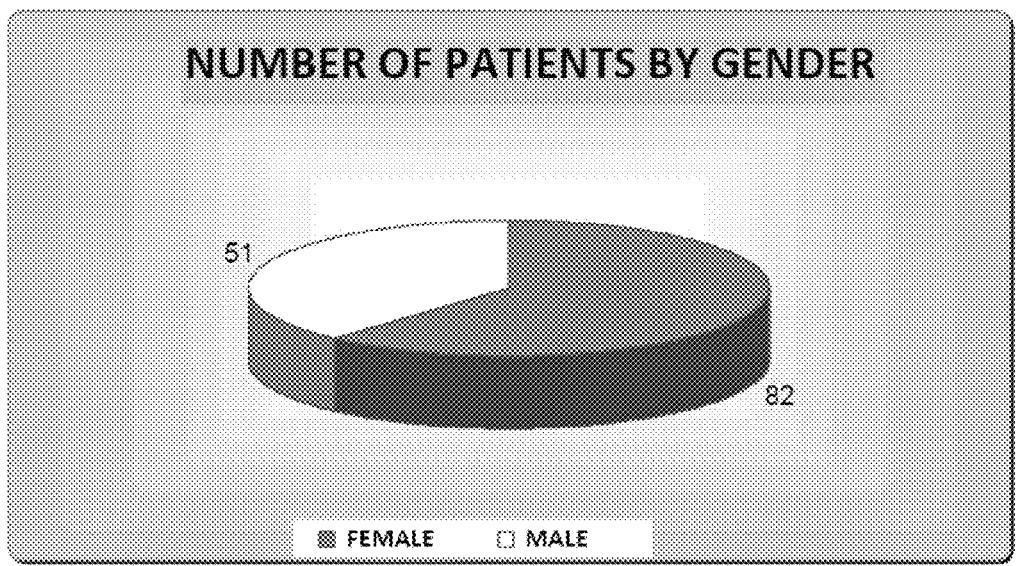
FIG. 33 reports the number of patients treated with the vaccine by gender, according to the study of clinical phases I and II in Example 4.

FIG. 33. It is shown that the annual incidence of cancer is higher in women than in men.

Figure 34:
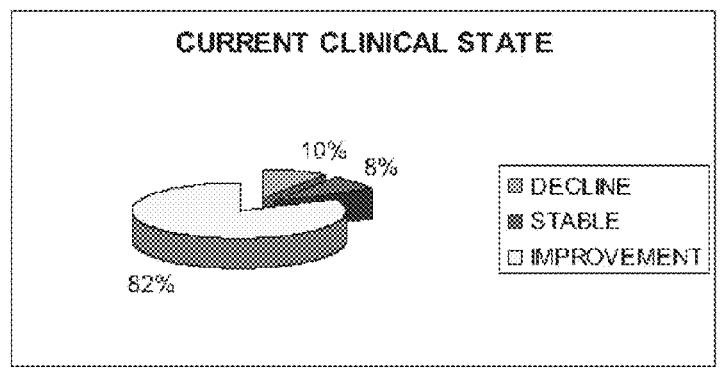
FIG. 34 shows the state of patients treated with the vaccine, with the corresponding percentage for: stability, improvement, and decline, according to the study of clinical phases I and II in Example 4.

FIG. 34. The clinical evolution of the patients studied showed that it was possible to provide stability during the treatment time (24 months), meaning that the vaccine did not let their injuries continue progressing despite the stage at which they were.

Figure 35:
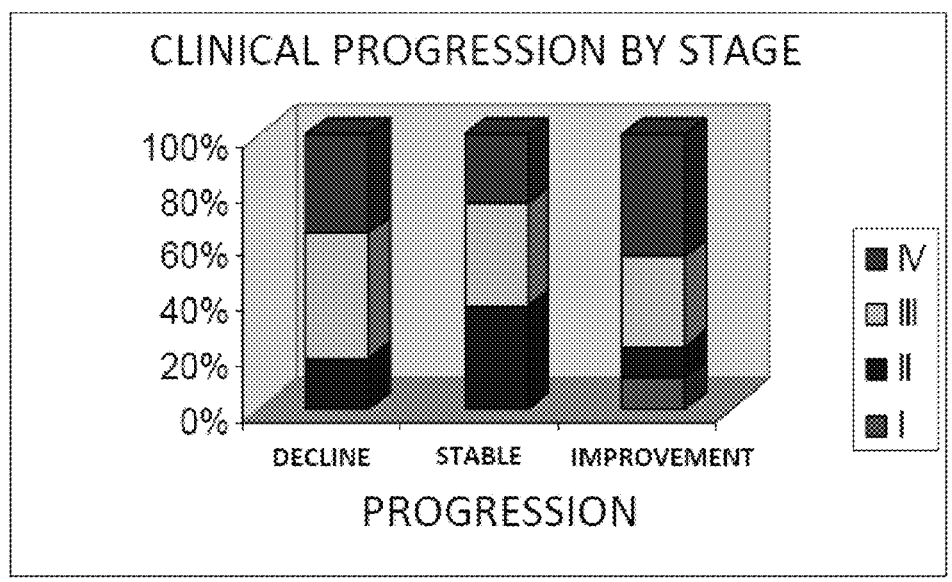
FIG. 35 indicates the clinical progression by stages I, II, III and IV, for patients treated with the vaccine, according to the study of clinical phases I and II in Example 4.

FIG. 35. It can be seen in this FIG. that clinical improvement occurred in the more advanced stages III and IV after the vaccine application, which implies that the vaccine was effective in certain types of advanced cancer.

Figure 36:
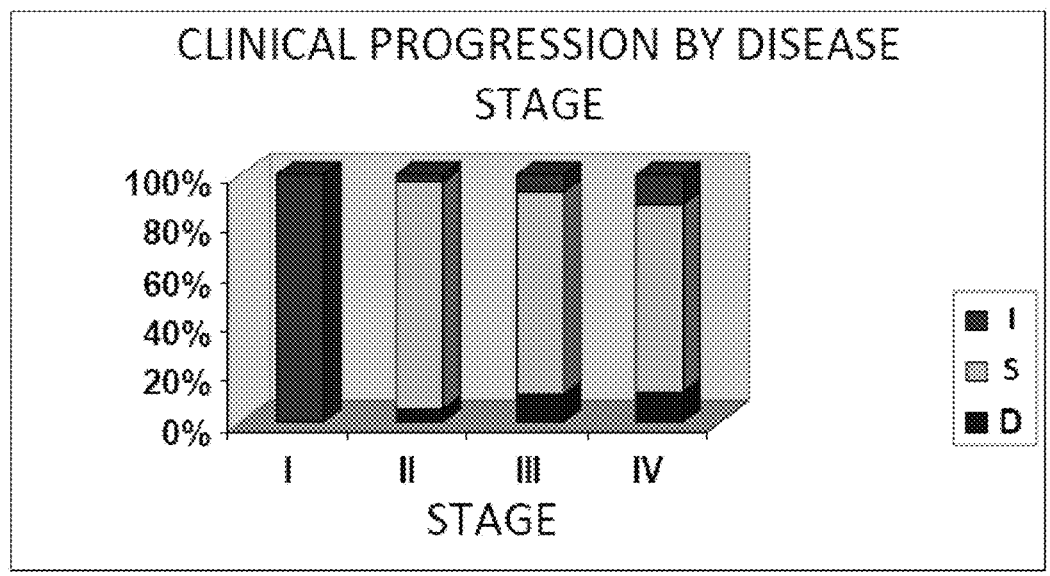
FIG. 36 reports the clinical progression by stages I, II, III and IV, for patients treated with the vaccine, with the corresponding percentage for: stability, improvement, and decline, according to the study of clinical phases I and II in Example 4.

FIG. 36. It can be observed in this FIG. that a large percentage of patients treated with the vaccine remained clinically stable during the study period (24 months), meaning that their disease did not progress more than 25%, nor did their lesions grow by more than that percentage, giving them quality of life and survival; however, a small percentage of patients continued progression, that is, the disease progressed compared to another small percentage for whom lesions decreased or improved and therefore their quality of life improved significantly.

Figure 37:
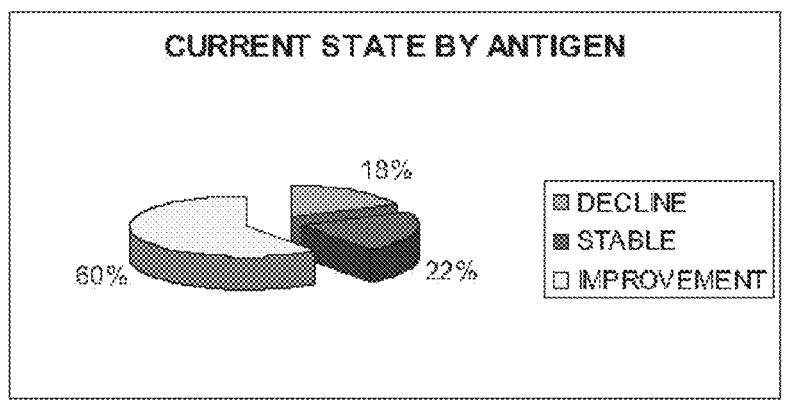
FIG. 37 shows the percentages of patients that show stability, improvement or decline after treatment with the vaccine, depending on the antigen, according to the study of clinical phases I and II in Example 4.
Figure 38:
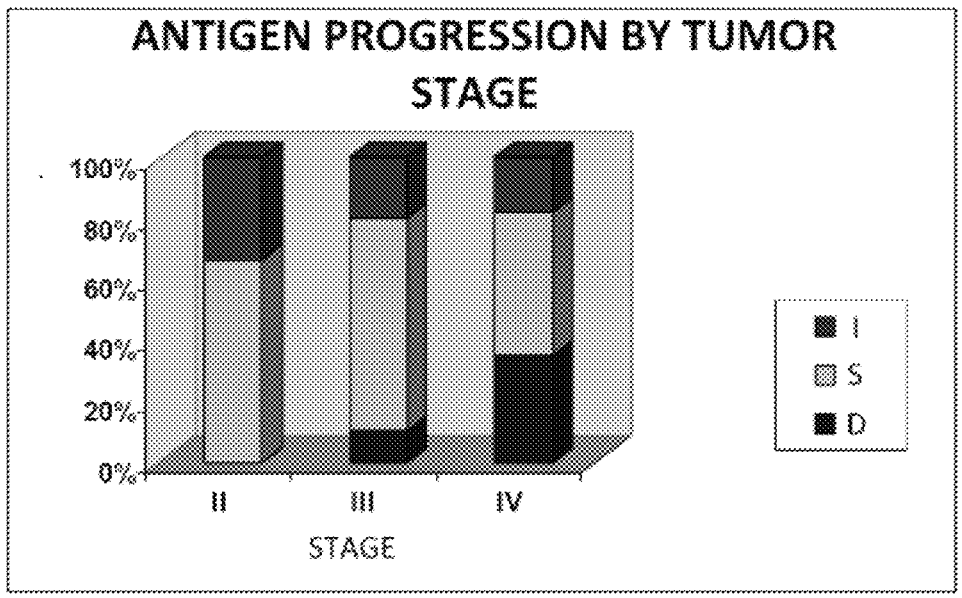
FIG. 38 shows the percentages of patients that show stability, improvement or decline after treatment with the vaccine, and corresponding to the evolution of the antigen by the stage of the tumor, according to the study of clinical phases I and II in Example 4.

FIGS. 37 and 38. The results of the antigen (tumor marker) before and during treatment showed that it remained stable for a large proportion, that it did not increase. This implies that the disease did not progress, while in a smaller percentage it remained active, meaning that the disease progressed. For another small percentage, this antigen was stabilized. Therefore the disease stopped being active.

Figure 39:
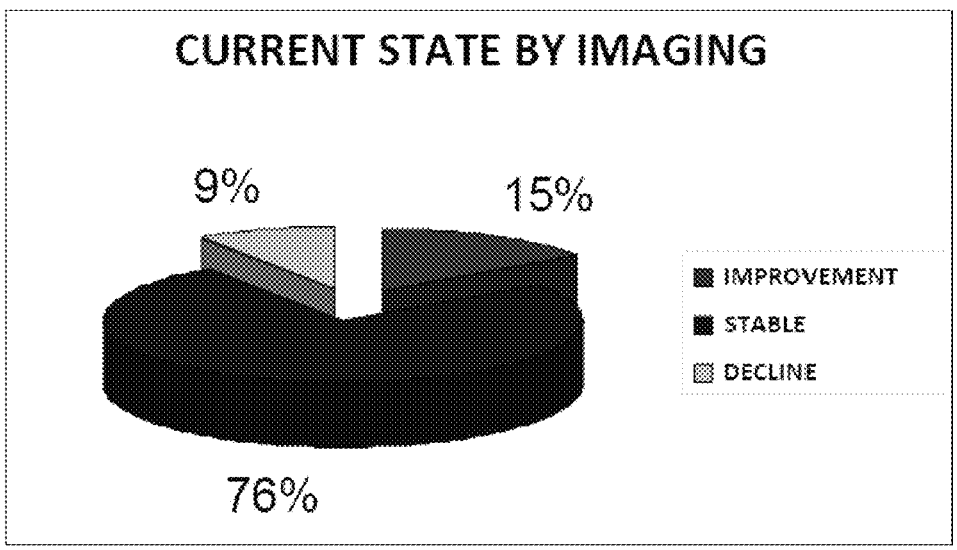
FIG. 39 reports the percentages of patients that show stability, improvement or decline after treatment with the vaccine, and corresponding to the diagnostic imaging, according to the study of clinical phases I and II in Example 4.
Figure 40:
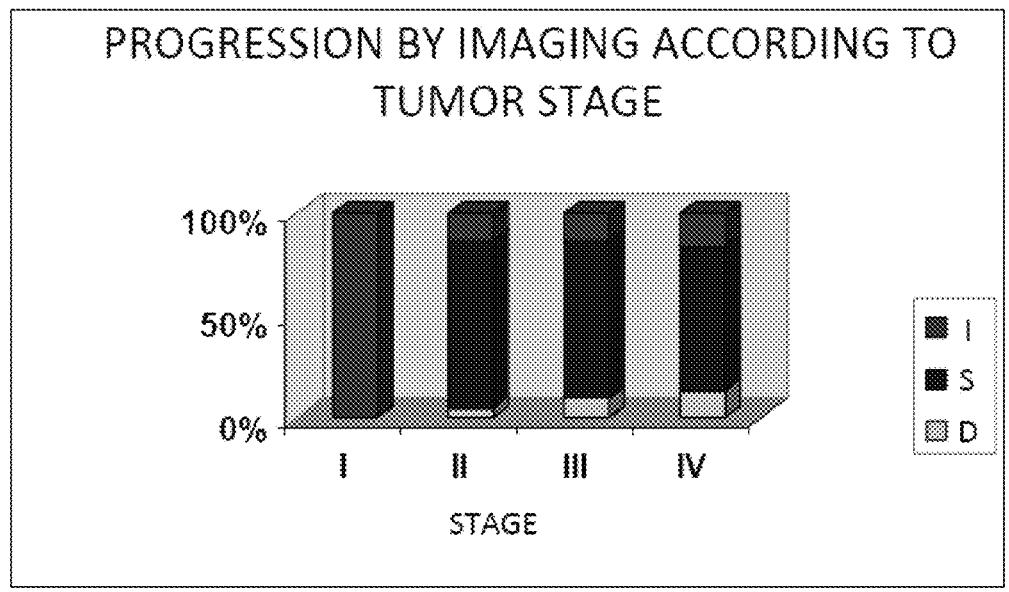
FIG. 40 reports the percentage of patients that show stability, improvement or decline after treatment with the vaccine, and corresponding to the diagnostic imaging by Stages I, II, III or IV, according to the study of clinical phases I and II in Example 4.

FIGS. 39 and 40. It was observed during the study of diagnostic imaging that 76% of patients remained stable, implying that the disease did not advance, while 15% improved, i.e. the lesions decreased in size or disappeared, and in 9% it continued to progress.

Figure 41:
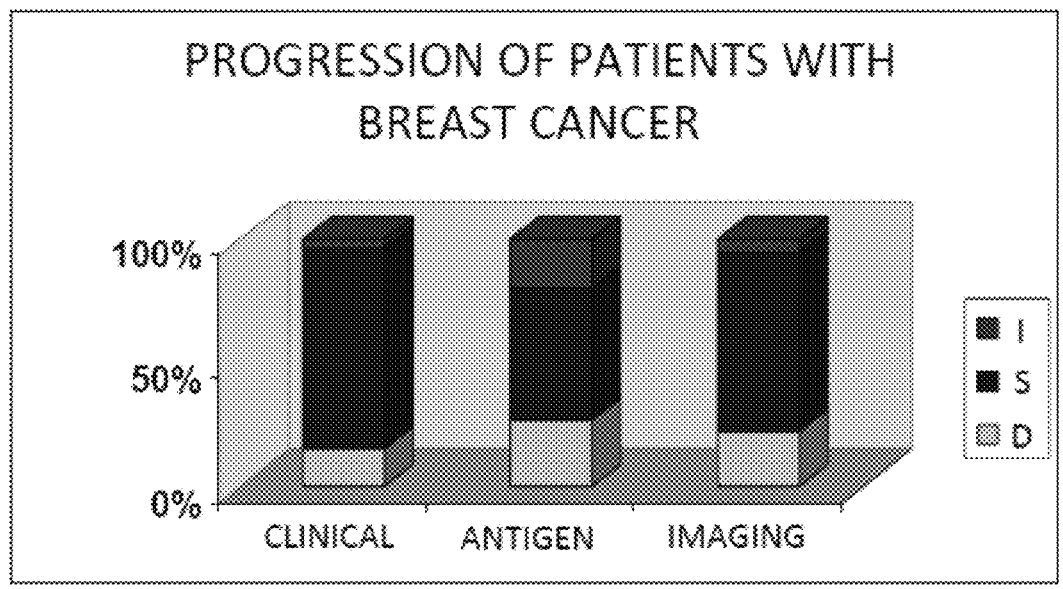
FIG. 41 reports the percentages of patients with breast cancer who show stability, improvement or decline after treatment with the vaccine, and corresponding to the diagnostic imaging by Stages I, II, III or IV, according to the study of clinical phases I and II in Example 4.

FIG. 41. After treatment with the vaccine, during the 24 months, breast cancer patients remained clinically stable, their antigen advanced and diagnostic images did not decline.

Figure 42:
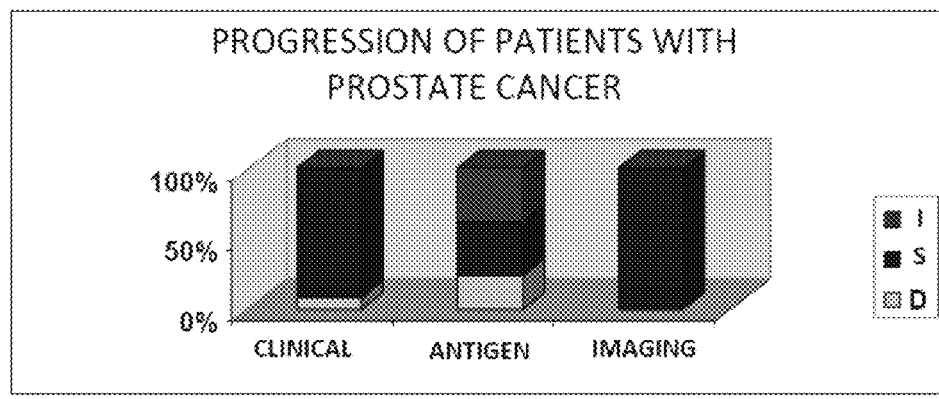
FIG. 42 reports the percentages of prostate cancer patients who show stability, improvement or decline after treatment with the vaccine, and corresponding to the diagnostic imaging by Stages I, II, III or IV, according to the study of clinical phases I and II in Example 4.

FIG. 42. It can be seen that patients with prostate cancer remained clinically stable during the treatment time, while the antigen improved, i.e. it normalized. This implies that both their disease and the diagnostic images were stable, meaning that their lesions did not continue to increase.

Figure 43:
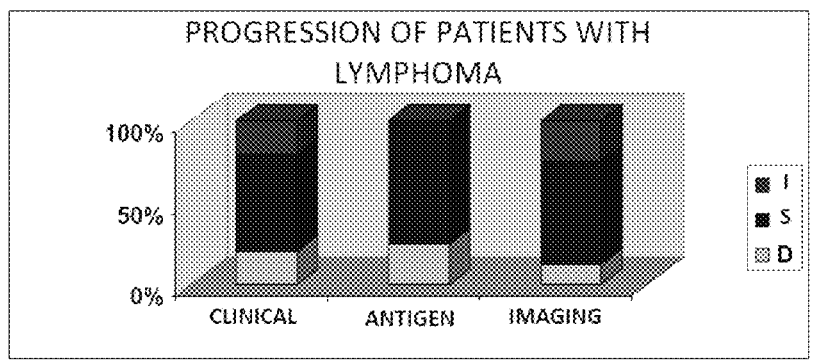
FIG. 43 reports the percentages of patients with lymphoma who show stability, improvement or decline after treatment with the vaccine, and corresponding to the diagnostic imaging by Stages I, II, III or IV, according to the study of clinical phases I and II in Example 4.

FIG. 43. Treatment with the vaccine in patients with Hodgkin lymphoma (HL) and non-Hodgkin lymphoma (NHL) showed patients remained stable in the disease, improving their diagnostic images in relation to the antigen and the quality of life.

Figure 44:
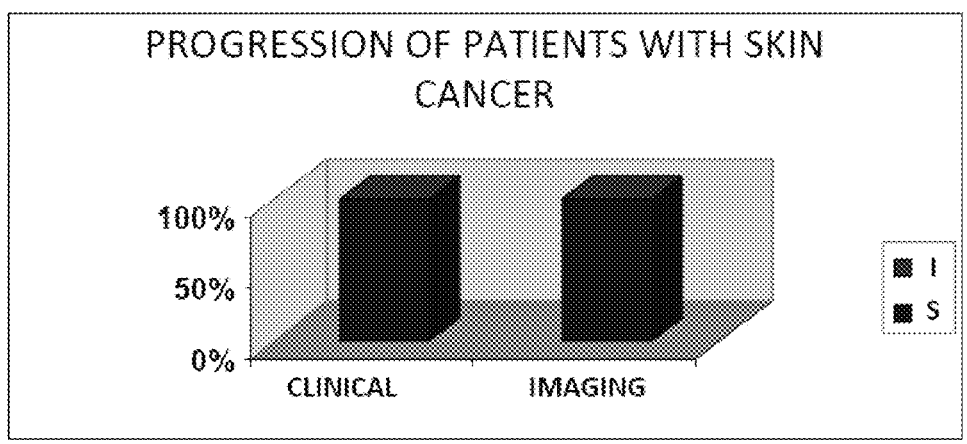
FIG. 44 reports the percentages of patients with skin cancer who show stability, improvement or decline after treatment with the vaccine, and corresponding to the diagnostic imaging by Stages I, II, III or IV, according to the study of clinical phases I and II in Example 4.

FIG. 44. Patients with malignant melanoma skin cancer, the second most aggressive cancer, and squamous cell and basal cell cancers, who were treated with the vaccine showed clinical stability. Diagnostic imaging during the study and treatment with the vaccine showed no cancer progression.

From the foregoing, it can be generally concluded that:
1. There is a blocking of metastasis (verified in vaccine-treated patients).
2. The immune system is reactivated (confirmed by lab tests).
3. There is tumor regression (verified by the clinical aspect and diagnostic imaging).
4. The quality of life of patients is improved (Karnofsky 90% to 100%).
5. Survival improves (life expectancy surpassed that of conventional treatments)

There are many possible embodiments of the present disclosure, of which only a few have been described herein. It is intended that the foregoing detailed description be regarded as illustrative rather than limiting, and that it be understood that it is the following claims, including all equivalents, that are intended to define the spirit and scope of this invention.

What is claimed is:

1. An autologous biological vaccine for treating cancer, consisting of:
   an active component corresponding to a tumor-associated antigen, in which the tumor associated antigen is overexpressed according to a type of cancer;
   a solvent;
   an attenuated virus strain C-154 of a parvovirus; and
   three amino acids (AA) corresponding to one essential amino acid and two nonessential amino acids.

2. A vaccine according to claim 1, wherein an active component for the tumor-associated antigen is CA 15-3.

3. A vaccine according to claim 1, wherein an active component for the tumor-associated antigen is CA 125.

4. A vaccine according to claim 1, wherein an active component for the tumor-associated antigen is CEA.

5. A vaccine according to claim 1, wherein an active component for the tumor-associated antigen is CA 19-9.

6. A vaccine according to claim 1, wherein an active component for the tumor-associated antigen is PSA.

7. A vaccine according to claim 1, wherein an active component for the tumor-associated antigen is the alpha fetoprotein.

8. A vaccine according to claim 1, wherein the solvent is distilled and deionized water.

9. A vaccine according to claim 1, wherein the essential amino acid is lysine and the two nonessential amino acids are proline and glycine.

10. A method for preparing an autologous biological vaccine, consisting of the following steps:
   a. providing a breast cancer tumor-associated antigen (ATA), in which the breast cancer tumor associated antigen is overexpressed in breast cancer tissue;
   b. providing an attenuated virus vaccine comprising strain C-154 of a parvovirus;
   c. placing 100 to 150 ml of distilled and deionized water in a container;
   d. centrifuging at a rate between 500 and 2000 rpm;
   e. adding one essential and two nonessential amino acids to the distilled and deionized water that is spinning, one at a time or all at once;
   f. adding 0.2 to 0.3 ml of the attenuated virus vaccine;
   g. adding between 0.1 ml and 0.2 ml of the tumor-associated antigen; and
   h. filtering.

11. A method according to claim 10, wherein the amount of distilled and deionized water used in step c is 100 ml.

12. A method according to claim 10, wherein the centrifuging speed in step d is 500 rpm.

13. A method according to claim 10, wherein step e consists of adding between 250 and 500 mg of the essential amino acid lysine, and adding between 500 and 700 mg of glycine and 250 to 350 mg of proline, the non-essential amino acids.

14. A method according to claim 13, wherein step e consists of adding about 400 mg of the essential amino acid lysine, about 700 mg of glycine and about 300 mg of proline.

15. A method according to claim 10, wherein in step f, 0.2 ml of DNA attenuated virus vaccine is added.

16. A method according to claim 10, wherein in step g, 0.2 ml of the tumor-associated antigen is added.

17. The method according to claim 10, wherein the filtered autologous biological vaccine is refrigerated at −4° C. after the step of filtering.

18. The method according to claim 10, wherein the container is stirred by placing a magnetic stirrer in the container.

* * * * *